(12) United States Patent
Voigt Pedersen

(10) Patent No.: US 10,575,104 B2
(45) Date of Patent: Feb. 25, 2020

(54) BINAURAL HEARING DEVICE SYSTEM WITH A BINAURAL IMPULSE ENVIRONMENT DETECTOR

(71) Applicant: GN HEARING A/S, Ballerup (DK)

(72) Inventor: Søren Christian Voigt Pedersen, Valby (DK)

(73) Assignee: GN HEARING A/S, Ballerup (DK)

( * ) Notice: Subject to any disclaimer, the term of this patent is extended or adjusted under 35 U.S.C. 154(b) by 7 days.

(21) Appl. No.: 15/837,440

(22) Filed: Dec. 11, 2017

(65) Prior Publication Data

US 2018/0176696 A1 Jun. 21, 2018

(30) Foreign Application Priority Data

Dec. 16, 2016 (DK) .................... 16204623.9

(51) Int. Cl.
| | | |
|---|---|---|
| *H04R 25/00* | (2006.01) | |
| *H04R 1/10* | (2006.01) | |
| *H04R 3/00* | (2006.01) | |
| *A61F 11/14* | (2006.01) | |
| *H04R 5/033* | (2006.01) | |

(52) U.S. Cl.
CPC ......... *H04R 25/505* (2013.01); *H04R 1/1083* (2013.01); *H04R 25/552* (2013.01); *A61F 11/14* (2013.01); *A61F 2011/145* (2013.01); *H04R 1/1008* (2013.01); *H04R 1/1041* (2013.01); *H04R 3/005* (2013.01); *H04R 5/033* (2013.01); *H04R 25/353* (2013.01); *H04R 25/356* (2013.01); *H04R 25/43* (2013.01); *H04R 25/554* (2013.01); *H04R 2201/107* (2013.01); *H04R 2225/41* (2013.01); *H04R 2225/43* (2013.01); *H04R 2420/01* (2013.01); *H04R 2430/03* (2013.01)

(58) Field of Classification Search
CPC .. A61F 11/14; A61F 2011/145; H04R 1/1008; H04R 1/1041; H04R 1/1083; H04R 3/005; H04R 5/033; H04R 25/43; H04R 25/356; H04R 25/353; H04R 25/505; H04R 25/552; H04R 25/554; H04R 2201/107; H04R 2225/41; H04R 2225/43; H04R 2420/01; H04R 2430/03
See application file for complete search history.

(56) References Cited

U.S. PATENT DOCUMENTS

| | | | |
|---|---|---|---|
| 2011/0144779 A1* | 6/2011 | Janse | G11B 20/10009 700/94 |
| 2015/0117660 A1* | 4/2015 | Fletcher | G10K 11/178 381/72 |
| 2017/0048609 A1* | 2/2017 | Schnell | H04R 1/1083 |

* cited by examiner

*Primary Examiner* — Brian Ensey
(74) *Attorney, Agent, or Firm* — Vista IP Law Group, LLP

(57) ABSTRACT

A hearing device and a method is provided that alleviate discomfort caused by sound impulses, such as a door slam, clinking of silverware, jangling of keys, etc., by converting sound into an audio signal, subjecting the audio signal to a frequency transformation, detecting presence of an impulse in the audio signal based on the frequency transformed audio signal, and processing the audio signal into a processed audio signal in response to detected presence of the impulse in the audio signal, converting the processed signal into an output sound signal, and emitting the output sound signal towards an eardrum of a human. The processing may involve reducing the gain of the output sound signal if an impulse is detected.

35 Claims, 16 Drawing Sheets

BINAURAL HEARING DEVICE SYSTEM WITH A BINAURAL IMPULSE ENVIRONMENT DETECTOR

RELATED APPLICATION DATA

This application claims priority to, and the benefit of, European Patent Application No. 16204623.9 filed on Dec. 16, 2016, pending. The entire disclosure of the above application is expressly incorporated by reference herein.

FIELD

A novel hearing device is provided with a binaural impulse environment detector.

BACKGROUND

For hearing instrument usage as well as hearing protection usage, there is a need for detecting and classifying an acoustic environment to be an impulse environment. An impulse environment is an acoustic environment where sounds of short duration, high energy and having very short rise times, are occurring with some frequency over time. An impulse environment may for example be experienced during a military training session with firearms, or during a canteen visit with noise from cutlery.

In impulse environments, users of hearing protection devices, hearing aids, headsets, etc., typically experience discomfort.

SUMMARY

There is a need for reliable detection of presence of an impulse environment in order to be able to automatically adjust the user's device to maximize comfort, speech intelligibility, etc.

A novel binaural hearing device system and a novel method of binaural signal processing are provided that alleviates discomfort caused by sound impulses. Sound impulses are sounds exhibiting high sound pressures during a short time period, such as a time period in the order of milliseconds, such as shorter than 10 milliseconds. The sound impulses may occur in an impulse environment which is a sound environment with occurrence of sound impulses at both ears of a person with some frequency over time.

The novel method of binaural signal processing, comprises the steps of converting sound into an audio signal at both ears of a human, detecting a presence of an impulse in each of the audio signals based on the respective audio signal, and processing each of the audio signals into a processed audio signal in response to the detected presence of the impulse in both audio signals, converting each of the processed signals into an output sound signal, and emitting each of the output sound signals towards an eardrum at both ears of the human.

The method may further comprise the step of dividing each of the audio signals into a plurality of frequency bands, and the step of detecting the presence of an impulse may comprise detecting the presence of the impulse in each of the audio signals based on the frequency-band divided audio signal.

The frequency bands may be warped frequency bands or non-warped frequency bands.

The step of dividing the audio signal into a plurality of frequency bands may comprise subjecting the audio signal to a frequency transformation, and the step of detecting presence of an impulse in the audio signal may be performed in the frequency domain.

The frequency transformation may be a warped frequency transformation.

The frequency transformation may be a Warped Fourier Transformation, a Warped Discrete Fourier Transformation, a Warped Fast Fourier Transformation, etc.

The warped frequency bands may correspond to the Bark frequency scale of the human ear.

The frequency transformation may be a non-warped frequency transformation.

The frequency transformation may be a Fourier Transformation, such as a Discrete Fourier Transformation, a Fast Fourier Transformation, etc.

The novel binaural hearing device system comprises a binaural hearing device with a first hearing device and a second hearing device, each of which comprises at least one microphone for provision of an audio signal in response to sound received at the at least one microphone in a sound environment, a signal processor that is adapted for processing the audio signal in accordance with a predetermined signal processing algorithm to generate a processed audio signal, a sound impulse detector that is adapted for detecting presence of an impulse in the audio signal and outputting an impulse detected signal indicating when an impulse is detected, and a receiver connected to an output of the signal processor for converting the processed audio signal into an output sound signal for emission towards an eardrum of a user, and a binaural impulse environment detector for binaural determination of presence of an impulse environment surrounding a user of the binaural hearing device system based on the impulse detected signal of the sound impulse detector of the first hearing device and the impulse detected signal of the sound impulse detector of the second hearing device.

The binaural impulse environment detector is configured for determination of presence of an impulse environment surrounding a user of the binaural hearing device system when the impulse detected signal of the sound impulse detector of the first hearing device and the impulse detected signal of the sound impulse detector of the second hearing device detect binaural, i.e. simultaneous, presence of sound impulses at both ears of the user with some frequency over time.

Signal Processing

Each of the first and second hearing devices comprises a signal processor adapted for processing of sound received by the hearing device in a way that is suitable for the intended use of the hearing device. For example, in a hearing aid the signal processor is adapted for compensation of the user's hearing loss. As is well known in the art, the processing of the signal processor is controlled by a signal processing algorithm having various parameters for adjustment of the actual signal processing performed. The gains in each of the frequency channels of a multi-channel hearing aid are examples of such parameters.

The flexibility of the signal processor is often utilized to provide a plurality of different algorithms and/or a plurality of sets of parameters of a specific algorithm. For example, various algorithms may be provided for noise suppression, i.e. attenuation of undesired signals and amplification of desired signals. Desired signals are usually speech or music, and undesired signals can be background speech, restaurant clatter, music (when speech is the desired signal), traffic noise, etc.

The different algorithms or parameter sets are typically included to provide comfortable and intelligible reproduced sound quality in different sound environments, such as speech, babble speech, restaurant clatter, music, traffic noise, etc. Audio signals obtained from different sound environments may possess very different characteristics, e. g. average and maximum sound pressure levels (SPLs) and/or frequency content. Therefore, in each of the first and second hearing devices, various sound environments may be associated with particular respective programs wherein a particular setting of algorithm parameters of a signal processing algorithm provides processed sound of optimum signal quality in a specific sound environment. A set of such parameters may typically include parameters related to broadband gain, corner frequencies or slopes of frequency-selective filter algorithms and parameters controlling e.g. knee-points and compression ratios of Automatic Gain Control (AGC) algorithms.

Consequently, the signal processor of the first and second hearing devices may be provided with a number of different programs, each program tailored to a particular sound environment or sound environment category and/or particular user preferences.

In a hearing aid, signal processing characteristics of each of these programs is typically determined during an initial fitting session in a dispenser's office and programmed into the hearing aid by activating corresponding algorithms and algorithm parameters in a non-volatile memory area of the hearing aid and/or transmitting corresponding algorithms and algorithm parameters to the non-volatile memory area.

In each of, or one of, the first and second hearing devices, the signal processor may be adapted for dividing the audio signal into a plurality of non-warped frequency bands, e.g. utilizing a filter bank, e.g. a filter bank with linear phase filters.

In each of, or one of, the first and second hearing devices, the signal processor may be adapted for dividing the audio signal into a plurality of warped frequency bands, e.g. utilizing a filter bank with warped filters.

In each of, or one of, the first and second hearing devices, the signal processor may be adapted for dividing the audio signal into the plurality of frequency bands by subjecting the audio signal to a frequency transformation, such as a Fourier Transformation, such as a Discrete Fourier Transformation, a Fast Fourier Transformation, etc., or a Warped Fourier Transformation, a Warped Discrete Fourier Transformation, a Warped Fast Fourier Transformation, etc.

The warped frequency bands of each of the signal processors of the first and second hearing devices may correspond to the Bark frequency scale of the human ear.

Signal processing in the novel binaural hearing device system may be performed by dedicated hardware or may be performed in one or more signal processors, or performed in a combination of dedicated hardware and one or more signal processors.

Signal processing performed by the binaural hearing device system may be performed by one common signal processor, for example located in a housing of one of the first and second hearing devices or in another housing of the binaural hearing device system or in another device, such as a hand-held device, such as a smartphone, a remote control, etc.

Signal processing may also be performed by a plurality of signal processors, each of which, or parts of which, may be located in a housing of one of the first and second hearing devices or in another housing of the binaural hearing device system or in another device, such as a hand-held device, such as a smartphone, a remote control, etc.

For example, each of the first and second hearing aids may have a housing that accommodates a hearing loss processor that is adapted to process the audio signal into a hearing loss compensated audio signal compensating for the hearing loss of the user and provided to the receiver for conversion into a sound signal for emission to the eardrum of a user, while the binaural impulse environment detector may be located in a smartphone communicating wirelessly with the first and second hearing devices.

As used herein, the terms "processor", "central processor", "hearing loss processor", "signal processor", "controller", "system", etc., are intended to refer to CPU-related entities, either hardware, a combination of hardware and software, software, or software in execution.

For example, a "processor", "signal processor", "controller", "system", etc., may be, but is not limited to being, a process running on a processor, a processor, an object, an executable file, a thread of execution, and/or a program.

By way of illustration, the terms "processor", "central processor", "hearing loss processor", "signal processor", "controller", "system", etc., designate both an application running on a processor and a hardware processor. One or more "processors", "central processors", "hearing loss processors", "signal processors", "controllers", "systems" and the like, or any combination hereof, may reside within a process and/or thread of execution, and one or more "processors", "central processors", "hearing loss processors", "signal processors", "controllers", "systems", etc., or any combination hereof, may be localized in one hardware processor, possibly in combination with other hardware circuitry, and/or distributed between two or more hardware processors, possibly in combination with other hardware circuitry.

Also, a signal processor (or similar terms) may be any component or any combination of components that is capable of performing signal processing. For examples, the signal processor may be an ASIC processor, a FPGA processor, a general purpose processor, a microprocessor, a circuit component, or an integrated circuit.

Binaural Impulse Environment Detector

With the binaural impulse environment detector, it is possible to distinguish between one-sided occurrences of impulses, i.e. sound impulses arriving at one of the ears of the user, but not at the other ear of the user, e.g. caused by wind noise, user button operations, scratching helmet, etc., and two-sided, binaural sound impulses occurring in an impulse environment surrounding the user, wherein sound impulses arrive binaurally, at both ears of the user, with similarities of parameters of the respective sound impulses arriving at each ear, such as duration, energy, rise time, fall time, frequency of occurrence, etc.

The binaural impulse environment detector is configured for determination of presence of an impulse environment surrounding a user of the binaural hearing device system when the impulse detected signal of the sound impulse detector of the first hearing device and the impulse detected signal of the sound impulse detector of the second hearing device detect binaural, i.e. simultaneous, presence of sound impulses at both ears of the user with some frequency over time.

The binaural impulse environment detector may be adapted for provision of outputs for each of the first and second hearing devices for selection of the signal processing algorithm of each of the respective signal processors of the first and second hearing devices so that the hearing devices of the binaural hearing device system perform coordinated processing of the audio signals. For example, sound impulses may be attenuated without affecting the user's sense of direction by coordinated signal processing parameter adjustment, e.g. gain adjustment, attack time adjustment, release time adjustment, etc., in the first and second hearing devices when the binaural impulse environment detector has determined presence of an impulse environment.

With monaural impulse environment detectors operating independent in the first and second hearing devices mounted at a respective ear of the user, in the event of one-sided occurrence of a sound impulse, e.g. a user push button press, a gain or time constant adjustment will be performed at one ear of the user, but not the other, leading to degraded spatial performance due to the distortion of the spatial cues contained in the audio signals.

Binaural Sound Environment Detector

The binaural hearing device system may also comprise a binaural sound environment detector for binaural determination of the sound environment surrounding a user of the binaural hearing device system based on at least one signal from the first hearing device and at least one signal from the second hearing device for provision of outputs for each of the first and second hearing devices for selection of the signal processing algorithm of each of the respective signal processors of the first and second hearing devices so that the first and second hearing devices of the binaural hearing device system perform coordinated sound processing.

The binaural sound environment detector may comprise the binaural impulse environment detector.

The binaural sound environment detector may be adapted for classifying the sound environment into a predetermined set of sound environment classes, such as speech, babble speech, music, traffic noise, impulse environment, such as restaurant clatter, etc.

Obtained classification results may be utilised in the first and second hearing devices to automatically select signal processing characteristics of the hearing device, e. g. to automatically switch to the most suitable signal processing algorithm for the environment in question.

Different signal processing algorithms available in the first and second hearing devices may change the signal characteristics significantly. Sound characteristics may however differ significantly at the two ears of a user, and individual determination of the sound environment at each ear of the user would thus differ, which could lead to undesired different signal processing of sounds for each of the ears of the user. This is avoided with the binaural sound environment detector that determines the sound environment binaurally, i.e. based on signals obtained at both ears of the user, whereby each of the hearing devices processes sound in response to a common determination of sound environment so that the binaural hearing device system is able to provide optimum sound quality, e.g. speech intelligibility, to the binaural hearing device user in various sound environments.

Also, binaural sound environment detection is more accurate than monaural detection since signals from both ears are taken into account.

Sound Impulse Suppressor

In each of, or one of, the first and second hearing devices, the signal processor may comprise a sound impulse suppressor adapted for attenuating the impulse by signal processing parameter adjustment, e.g. by gain adjustment, attack time adjustment, release time adjustment, etc., in response to detection of the impulse by the sound impulse detector.

For example, in a sound environment without sound impulses, the signal processors of the first and second hearing devices may operate in accordance with a signal processing algorithm wherein the sound impulse suppressors operate monaurally, i.e. independent of sound received at the other ear of the user, for fast, preferably instantaneous, suppression of sound impulses detected by the respective sound impulse detector until the binaural impulse environment detector determines that the sound environment has changed to a sound environment with occurrences of sound impulses and controls the signal processors of the first and second hearing devices to operate in accordance with another signal processing algorithm for optimum signal processing in the impulse environment and so that the hearing devices of the binaural hearing device system perform coordinated processing of the audio signals. For example, sound impulses may be attenuated without affecting the user's sense of direction by coordinated signal processing parameter adjustment, e.g. gain adjustment, attack time adjustment, release time adjustment, etc., in the first and second hearing devices. The selected signal processing algorithm may for example control the sound impulse suppressors of the first and second hearing devices to lower the resulting gain of the signal processors of the first and second hearing devices by the same amount to avoid distortion of spatial cues contained in the processed audio signals, whereby the user can maintain sense of direction.

In each of, or one of, the first and second hearing devices, the sound impulse suppressor may be adapted for reducing gain with the same amount in a plurality of the frequency bands of the signal processor.

In each of, or one of, the first and second hearing devices, the sound impulse suppressor may be adapted for reducing gain individually in a plurality of the frequency bands of the signal processor.

In each of, or one of, the first and second hearing devices, the sound impulse suppressor may be adapted for reducing gain as a function of broad-band power when presence of a sound impulse is detected.

In each of, or one of, the first and second hearing devices, the sound impulse suppressor may be adapted for reducing gain to 0 dB when presence of a sound impulse is detected.

In each of, or one of, the first and second hearing devices, the sound impulse suppressor may be adapted for attenuating the impulse in such a way that the receiver does not emit sound, or substantially does not emit sound, originating from the impulse.

In each of, or one of, the first and second hearing devices, the sound impulse suppressor may be adapted for attenuating the impulse in such a way that the user hears the corresponding sound impulse as if the user did not wear the hearing device.

In each of, or one of, the first and second hearing devices, signal processing parameters of the sound impulse suppressor may be adjustable in accordance with user inputs.

Sound Impulse Detector

In each of, or one of, the first and second hearing devices, the sound impulse detector may be adapted for dividing the audio signal into a plurality of non-warped frequency bands, e.g. utilizing a filter bank, e.g. a filter bank with linear phase filters, and for detecting the presence of an impulse in the audio signal based on the divided audio signal.

In each of, or one of, the first and second hearing devices, the sound impulse detector may be adapted for dividing the audio signal into a plurality of warped frequency bands, e.g. utilizing a filter bank with warped filters, and for detecting the presence of an impulse in the audio signal based on the frequency-divided audio signal.

In each of, or one of, the first and second hearing devices, the sound impulse detector may be adapted for dividing the audio signal into the plurality of frequency bands by subjecting the audio signal to a frequency transformation, such as a Fourier Transformation, such as a Discrete Fourier Transformation, a Fast Fourier Transformation, etc., or a Warped Fourier Transformation, a Warped Discrete Fourier Transformation, a Warped Fast Fourier Transformation, etc., and for detecting the presence of an impulse in the audio signal in the frequency domain.

In each of, or one of, the first and second hearing devices, the warped frequency bands of the sound impulse detector may correspond to the Bark frequency scale of the human ear.

In each of, or one of, the first and second hearing devices, the frequency bands of the sound impulse detector may be different from the frequency bands of the signal processor, and if the sound impulse detector forms part of the signal processor, the frequency bands of the sound impulse detector may be different from the frequency bands of other parts of the signal processor, such as the frequency bands of the sound impulse suppressor.

For example, the frequency bands of the sound impulse suppressor may be warped frequency bands while the frequency bands of the sound impulse detector may be non-warped frequency bands.

In each of, or one of, the first and second hearing devices, the sound impulse detector may be adapted for determining a signal level $S_0$ of the audio signal in a frequency band $F_i$ at a time $t_0$ and comparing the determined signal level $S_0$ with a signal level $S_{-1}$ based on at least one previously determined signal level in the frequency band $F_i$ when determining presence of the impulse in the audio signal.

In each of, or one of, the first and second hearing devices, the sound impulse detector may be adapted for determining presence of the impulse in the audio signal when the ratio between the signal level $S_0$ of the audio signal in a frequency band $F_i$ determined at time $t_0$ and the signal level $S_{-1}$ based on at least one previously determined signal level in the frequency band $F_i$ is greater than a predetermined threshold $Th_i$ for a predetermined number N of frequency bands $F_i$. In the following, the predetermined threshold $Th_i$ is also denoted the impulse gradient threshold.

In each of, or one of, the first and second hearing devices, the signal level may be the sound pressure level (SPL) in dB, i.e. the ratio of the root mean square sound pressure and a reference sound pressure of 20 µPa in dB.

Compared to speech, a sound impulse causing discomfort to a human typically exceeds the predetermined threshold in a large number of frequency bands, such as in a number of frequency bands larger than half the total number of frequency bands, for example 10 for a total number of 17 frequency bands, i.e. N may be equal to 10 for a total number of 17 frequency bands.

In each of, or one of, the first and second hearing devices, the threshold may be equal to 10 dB for all frequency bands.

In each of, or one of, the first and second hearing devices, the sound impulse detector may be adapted for operation in response to the sound environment determined by the binaural sound environment detector, for example the threshold $Th_i$ may be a function of the sound environment determined by the binaural sound environment detector.

In each of, or one of, the first and second hearing devices, a broad-band power level may also be included in the determination of presence of an impulse in order to further distinguish presence of an impulse over the on-set of speech. For example, determination of presence of an impulse may require that the total sound pressure level of the frequency transformed audio signal is larger than a predetermined threshold, such as 75 $dB_{SPL}$, 80 $dB_{SPL}$, etc.

In each of, or one of, the first and second hearing devices, the predetermined threshold value may be adjusted in accordance with user preferences, as explained below in connection with table 1 which is reproduced from W. O. Olsen: "Average speech levels and spectra in various speaking/listening conditions, a summary of the Pearson, Bennett, Fidell (1977) report," American Journal of Audiology, vol. 7, pp. 21-25, 1998.

Table 1 below shows the speech levels (non-weighted SPL) of casual, normal, raised, loud, and shouted speech by males, females, and children:

TABLE 1

|  | Casual | Normal | Raised | Loud | Shouted |
| --- | --- | --- | --- | --- | --- |
| Females | 54 | 58 | 65 | 72 | 82 |
| Males | 56 | 61 | 68 | 77 | 89 |
| Children | 56 | 61 | 67 | 75 | 82 |

In each of, or one of, the first and second hearing devices, the sound impulse suppressor may be adapted for attenuating the impulse with an amount that is a function of the sound environment class determined by the binaural sound environment detector.

In each of, or one of, the first and second hearing devices, various signal processing parameters, such as detection thresholds, attenuation levels, etc., of the novel sound impulse detector and sound impulse suppressor may be adjustable in accordance with user inputs.

Hearing Devices

The binaural hearing device may comprise a data interface for transmission of data to a hand-held device.

The data interface may be a wired interface, e.g. a USB interface, or a wireless interface, such as a Bluetooth interface, e.g. a Bluetooth Low Energy interface.

The binaural hearing device may comprise an audio interface for reception of an audio signal from a hand-held device.

The audio interface may be a wired interface or a wireless interface.

The data interface and the audio interface may be combined into a single interface, e.g. a USB interface, a Bluetooth interface, etc.

The binaural hearing device may for example have a Bluetooth Low Energy data interface for exchange of data between the binaural hearing device and the hand-held device, and a wired audio interface for transmission of the audio signal.

The binaural hearing device may comprise one or more ambient microphones for receiving ambient sound for user selectable transmission towards at least one of the ears of the user.

In the event that the binaural hearing device provides a sound proof, or substantially, sound proof, transmission path for sound emitted by the receiver(s) of the hearing device towards the ear(s) of the user, the user may be acoustically disconnected in an undesirable way from the surroundings. This may for example be dangerous when moving in traffic.

The binaural hearing device may have a user interface, e.g. a push button, so that the user can switch the microphone on and off as desired thereby connecting or disconnecting the ambient microphone and one receiver or loudspeaker of the binaural hearing device.

The binaural hearing device may have a mixer with an input connected to an output of the one or more ambient microphones and another input connected to another source of an audio signal, e.g. the hand-held device, supplying an audio signal, and an output providing an audio signal that is a weighted combination of the two input audio signals.

The user input may further include means for user adjustment of the weights of the combination of the two input audio signals, such as a dial, or a push button for incremental adjustment.

The binaural hearing device may have a threshold detector for determining the loudness of the ambient signal received by the ambient microphone, and the mixer may be adapted for including the output of the ambient microphone signal in its output signal only when a certain threshold is exceeded by the loudness of the ambient signal.

Further ways of controlling audio signals from an ambient microphone and a voice microphone is disclosed in US 2011/0206217 A1.

Hearing Aid

The binaural hearing device system may be a binaural hearing aid system, wherein the binaural hearing device is a binaural hearing aid, wherein each of the first and second hearing devices is a hearing aid, such as a BTE, RIE, ITE, ITC, or CIC, etc., hearing aid, comprising a hearing loss processor that is adapted to process the audio signal in accordance with a predetermined signal processing algorithm to generate a hearing loss compensated audio signal compensating a hearing loss of a user.

The hearing loss processor may comprise a dynamic range compressor adapted for compensating the hearing loss including loss of dynamic range.

The hearing loss processor may form part of the signal processor.

Hearing impaired persons are, compared to persons with normal hearing, more susceptible to discomfort when subjected to sound impulses of high sound pressure levels.

A dynamic range compressor, in short "a compressor", in a hearing aid, utilizes dynamic sound level compression with time constants that are sufficiently long to avoid distortion of temporal characteristics of speech. The associated recruitment effect alleviated with a hearing aid increases the discomfort caused by sound impulses with high energy.

Typically, a hearing impaired human suffering from sensorineural hearing loss experiences a loss of hearing sensitivity that is 1) frequency dependent and 2) dependent upon the loudness of sound at an ear.

Thus, a hearing impaired human may be able to hear certain frequencies, e.g., low frequencies, as well as a human with normal hearing, while other frequencies are not heard as well. Typically, hearing impaired humans experience loss of hearing sensitivity at high frequencies.

At frequencies with reduced sensitivity, the hearing impaired human is often able to hear loud sounds as well as the human with normal hearing, but unable to hear soft sounds with the same sensitivity as the human with normal hearing. Thus, the hearing impaired human suffers from a loss of dynamic range.

A dynamic range compressor in a hearing aid compresses the dynamic range of sound arriving at an ear of the hearing impaired human to match the residual dynamic range of the human in question. The degree of dynamic hearing loss of the hearing impaired human may be different in different frequency bands.

The slope of the input-output compressor transfer function is referred to as the compression ratio. The compression ratio required by a human may not be constant over the entire input power range, i.e. typically the compressor characteristic has one or more knee-points.

Thus, dynamic range compressors may be adapted to perform differently in different frequency bands, thereby accounting for the frequency dependence of the hearing loss of the human in question. Such a multiband or multichannel compressor divides an input signal into two or more frequency bands or frequency channels and then compresses each frequency band or channel separately.

The multiband or multichannel compressor may divide the input signal into two or more warped frequency bands or frequency channels.

The dynamic range compressors further have attack and release time constants. The attack time constant determines the time it takes for the compressor to react at the onset of a loud sound. That is, the time it takes to turn down the gain. The release time constant determines the time it takes for the system to turn up the gain again after the loud sound has terminated. Most often the attack time is quite short (<5 milliseconds) with the release time being longer (anywhere from 15 to hundreds of milliseconds).

The parameters of the compressor, such as compression ratio, positions of knee-points, attack time constant, release time constant, etc. may be different for each frequency band.

Dynamic range compressors are fitted to the hearing loss of the human by adjustment of compressor parameters in accordance with accepted fitting rules and based on hearing thresholds determined for the human.

EP 1 448 022 A discloses a hearing aid with a multiband compressor.

In each of, or one of, the first and second hearing devices, the sound impulse suppressor may be adapted for performing signal processing parameter adjustments, e.g. gain adjustment, attack time adjustment, release time adjustment, etc., based on gain settings of the hearing loss processor and/or the compressor.

Headset, Headphone, Etc.

The binaural hearing device may be a headset, headphone, earphone, ear defender, or earmuff, etc., such as an Ear-Hook, In-Ear, On-Ear, Over-the-Ear, Behind-the-Neck, Helmet, or Headguard, etc.

The binaural hearing device may be a headset or a headphone having a headband carrying two earphones. The headband is intended to be positioned over the top of the head of the user as is well-known from conventional headsets and headphones.

The signal processor, or one or more parts of the signal processor, of the binaural hearing device system may be accommodated in the headband of the binaural hearing device. For example, the binaural impulse environment detector may be accommodated in the headband of the binaural hearing device.

The binaural hearing device may have a neckband carrying two earphones. The neckband is intended to be positioned behind the neck of the user as is well-known from conventional neckband headsets and headphones.

The signal processor, or one or more parts of the signal processor, of the binaural hearing device system may be accommodated in the neckband of the binaural hearing device. For example, the binaural impulse environment detector may be accommodated in the neckband of the binaural hearing device.

Hand-held Device

The binaural hearing device system may comprise a device separate from the binaural hearing device, such as a hand-held device, such as a remote control for the binaural hearing device, a hand-held computer, such as a smartphone, a tablet computer, a PDA, etc., and adapted to communicate with the binaural hearing device through a wired interface and/or through a wireless interface.

The signal processor, or one or more parts of the signal processor, of the binaural hearing device system may be accommodated in the hand-held device. For example, the binaural impulse environment detector, or the binaural sound environment detector with the binaural impulse environment detector, may be accommodated in the hand-held device.

The hand-held device may comprise a data interface for reception and transmission of data to and from the binaural hearing device.

The data interface may be a wired interface, e.g. a USB interface, or a wireless interface, such as a Bluetooth interface, e.g. a Bluetooth Low Energy interface.

The hand-held device may comprise an audio interface for transmission, and optional reception, of an audio signal to, and optionally from, the binaural hearing device.

The audio interface may be a wired interface or a wireless interface.

For example, the binaural hearing device may be connected to the hand-held device with a cord providing a wired audio interface for transmission of speech and music from the hand-held device to the binaural hearing device.

The data interface and the audio interface may be combined into a single interface, e.g. a USB interface, a Bluetooth interface, etc.

The hand-held device may for example have a Bluetooth Low Energy data interface for reception of the impulse detected signal of the sound impulse detector of the first hearing device and the impulse detected signal of the sound impulse detector of the second hearing device and for transmission of the outputs for each of the first and second hearing devices for selection of the appropriate signal processing algorithm of each of the respective signal processors of the first and second hearing devices based on determination of presence of an impulse environment surrounding the user of the binaural hearing device system.

The user may use a user interface of the hand-held device to control the binaural hearing device, e.g. for selection of a specific signal processing algorithm, or for adjustment of a signal processing parameter, such as the volume, the amount of attenuation of sound impulses, etc.

A binaural hearing device system for a user, includes: a first hearing device and a second hearing device, each of which comprises: at least one microphone for provision of an audio signal in response to sound received at the at least one microphone in a sound environment; a signal processor that is configured to process the audio signal in accordance with a signal processing algorithm to generate a processed audio signal; a sound impulse detector configured to detect a presence of an impulse in the audio signal, and to output an impulse detected signal; and a receiver configured to provide an output sound signal based on the processed audio signal for emission towards an eardrum of the user of the binaural hearing device system; and a binaural impulse environment detector for binaural determination of a presence of an impulse environment surrounding the user of the binaural hearing device system based on the impulse detected signal of the sound impulse detector of the first hearing device and the impulse detected signal of the sound impulse detector of the second hearing device.

Optionally, the binaural impulse environment detector is configured for provision of outputs for the first and second hearing devices for selection of the respective signal processing algorithms of the respective signal processors in the respective first and second hearing devices so that the first and second hearing devices perform coordinated processing of the audio signals.

Optionally, the binaural hearing device system further includes a binaural sound environment detector for binaural determination of the sound environment surrounding the user of the binaural hearing device system based on at least one signal from the first hearing device and at least one signal from the second hearing device.

Optionally, the binaural sound environment detector comprises the binaural impulse environment detector.

Optionally, the signal processor of the first hearing device comprises a sound impulse suppressor configured to attenuate the impulse in the audio signal of the first hearing device by signal processing parameter adjustment.

Optionally, the signal processing parameter adjustment is based on a user input.

Optionally, the sound impulse detector of the first hearing device is configured to divide the audio signal of the first hearing device into a plurality of frequency bands, and to detect the presence of the impulse in the audio signal of the first hearing device based on the frequency-divided audio signal.

Optionally, a signal processing parameter of the sound impulse detector of the first hearing device is adjustable in accordance with a user input.

Optionally, the signal processor of the first hearing device comprises a sound impulse suppressor; and wherein at least one of the sound impulse detector and the sound impulse suppressor in the first hearing device is adjustable in accordance with a sound environment class determined by the binaural sound environment detector in the first hearing device.

Optionally, the signal processor of each of the first hearing device and the second hearing device comprises a hearing loss processor configured to compensate a hearing loss of the user.

Optionally, the hearing loss processor of each of the first hearing device and the second hearing device comprises a dynamic range compressor configured to compensate the hearing loss including loss of dynamic range.

Optionally, the signal processor of each of the first hearing device and the second hearing device is configured to perform a gain adjustment based on a gain setting of the hearing loss processor of the respective one of the first hearing device and the second hearing device.

Optionally, each of the first hearing device and the second hearing device is a hearing protector comprising a passive dampener for dampening sound.

A method of binaural signal processing includes: converting sound into a first audio signal and a second audio signal for respective ears of a user; detecting a presence of an impulse in each of the first and second audio signals; and processing each of the first and second audio signals into a processed audio signal in response to the detected presence of the impulse in the respective one of the first and second audio signals; converting each of the processed signals into an output sound signal; and emitting each of the output sound signals towards an eardrum of the user.

Optionally, the method further includes reducing a gain of the processed audio signal in response to the detected presence of the impulse in each of the first and second audio signals.

BRIEF DESCRIPTION OF THE DRAWINGS

Other and further aspects and features will be evident from reading the following detailed description of the embodiments.

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

In the drawings:

FIG. 1 shows a binaural hearing device in the form of a headset,

FIG. 2 shows a binaural hearing device in the form of a binaural hearing aid,

FIG. 3 shows a block diagram of a binaural hearing device system,

FIG. 4 shows another block diagram of a binaural hearing device system,

FIG. 5 shows yet another block diagram of a binaural hearing device system,

Figure 6:
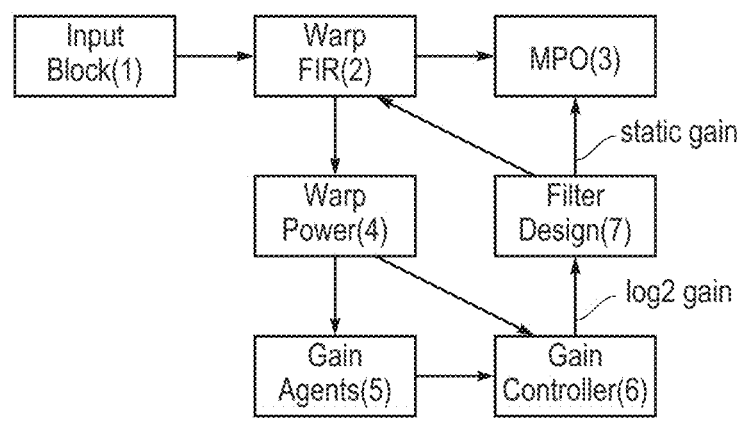
Figure 7:
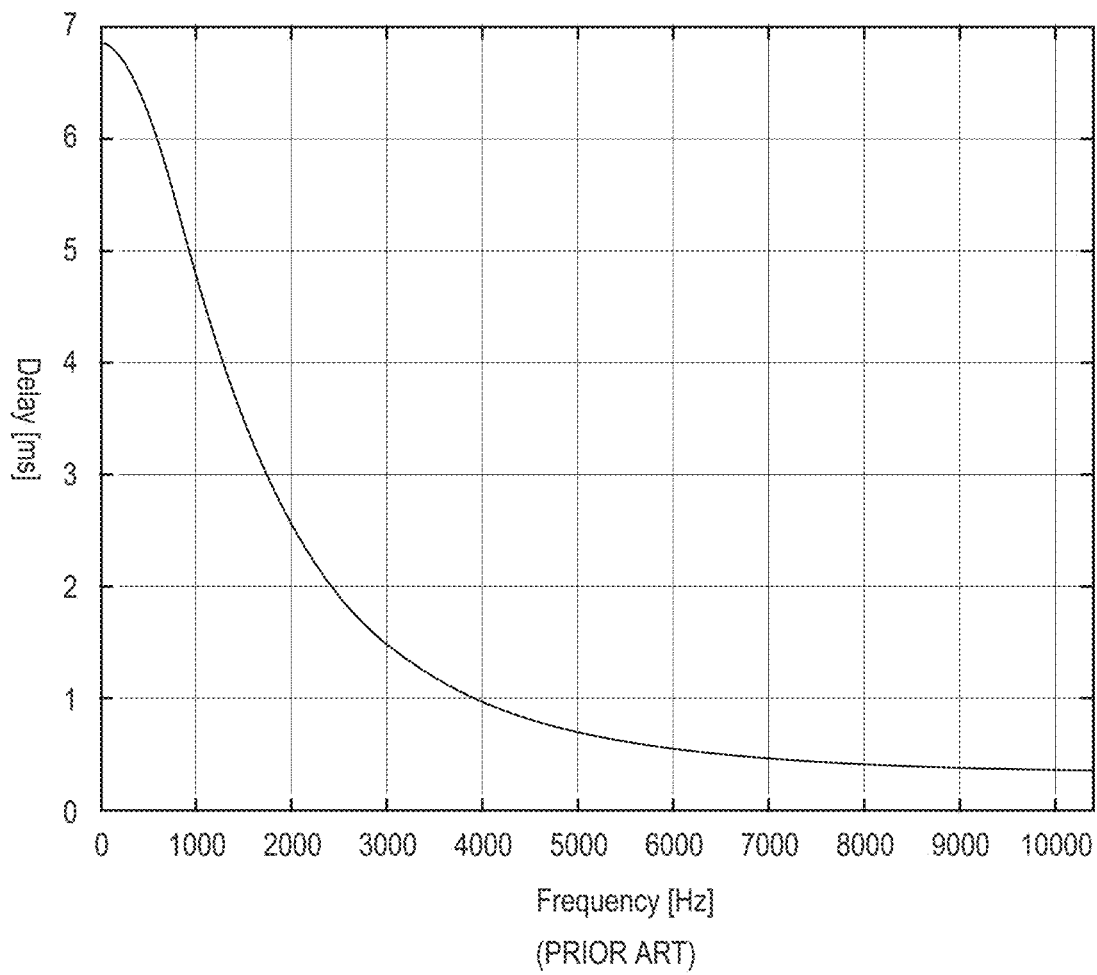
Figure 8:
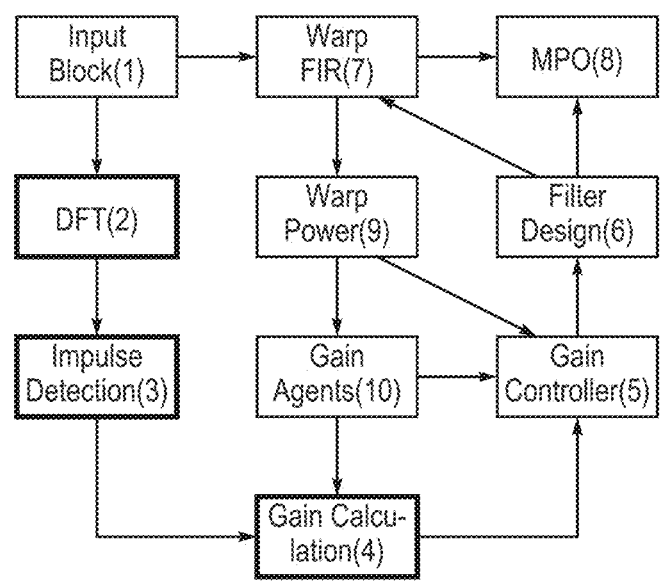
Figure 9:
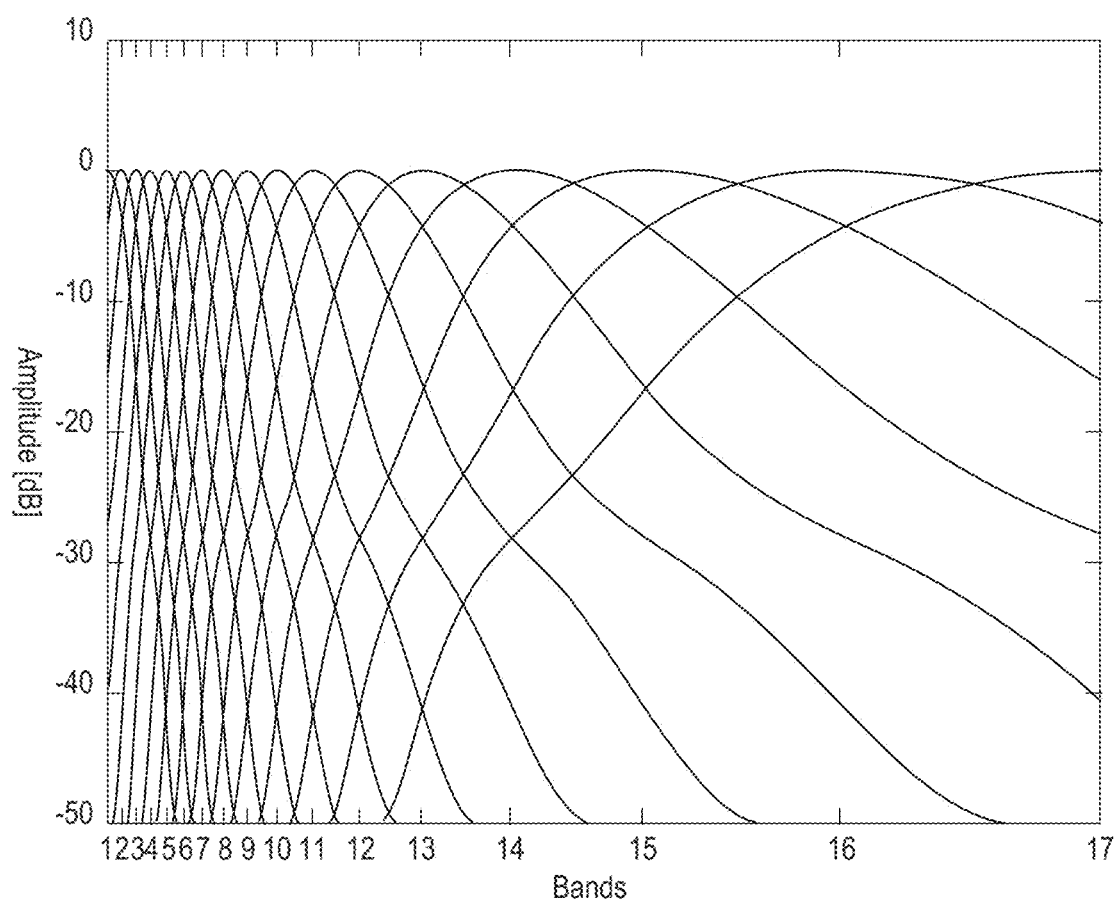
Figure 10:
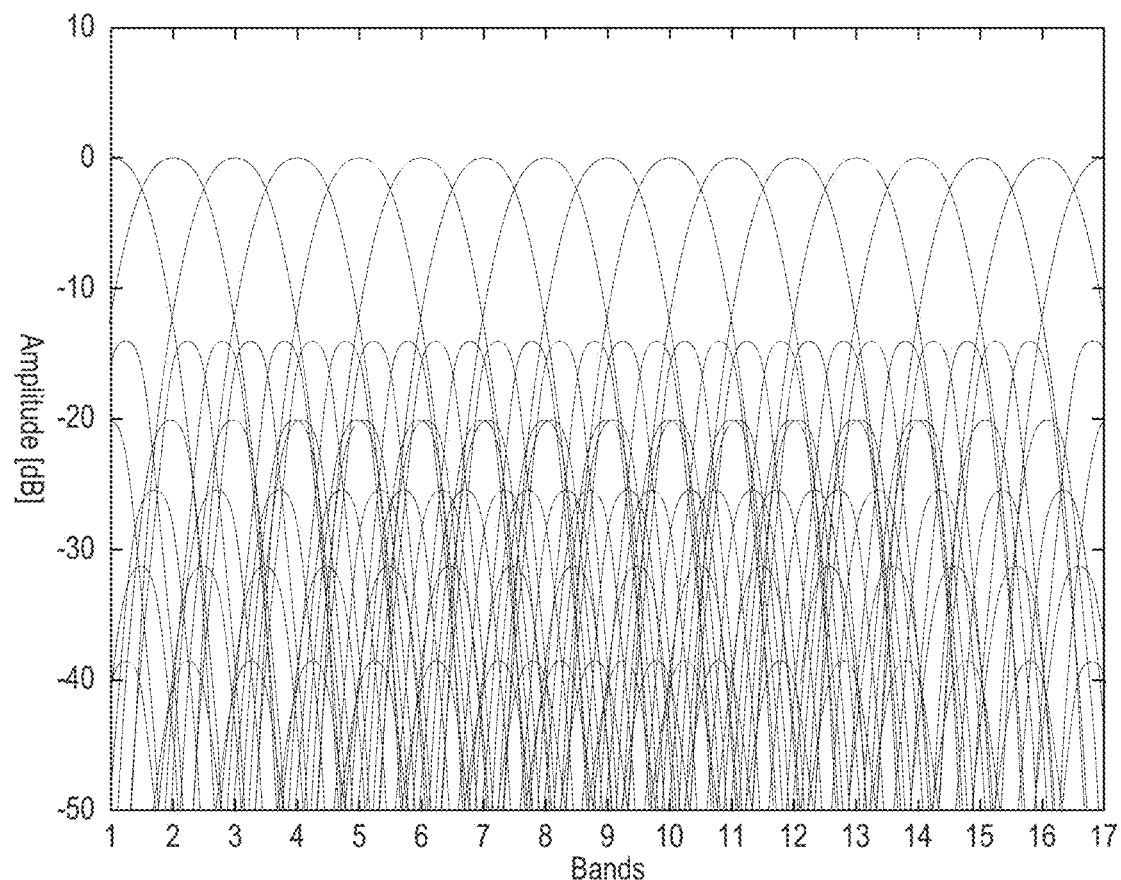
Figure 11:
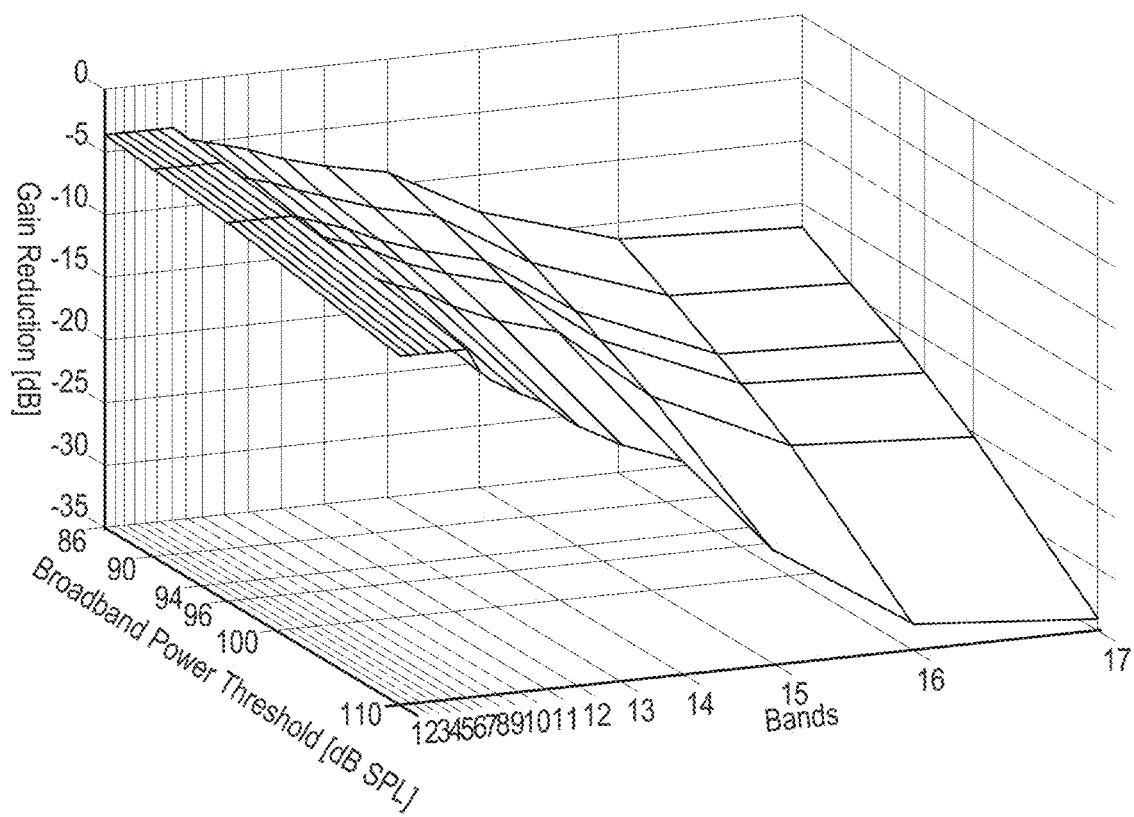
Figure 12A:
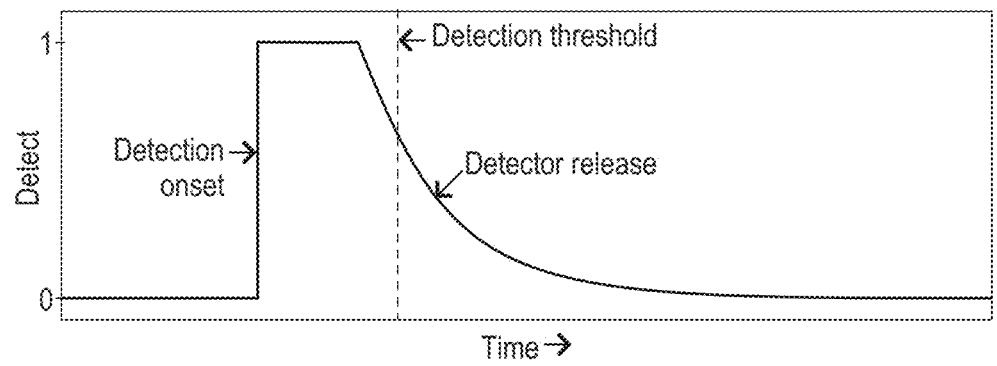
Figure 12B:
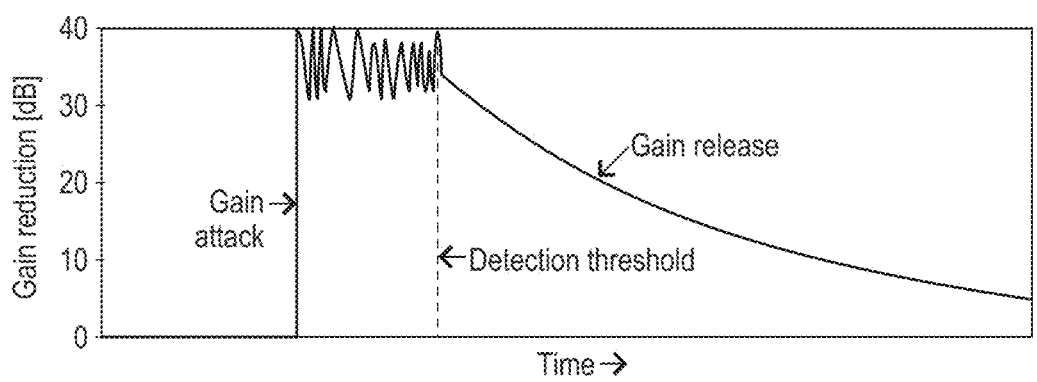
Figure 13:
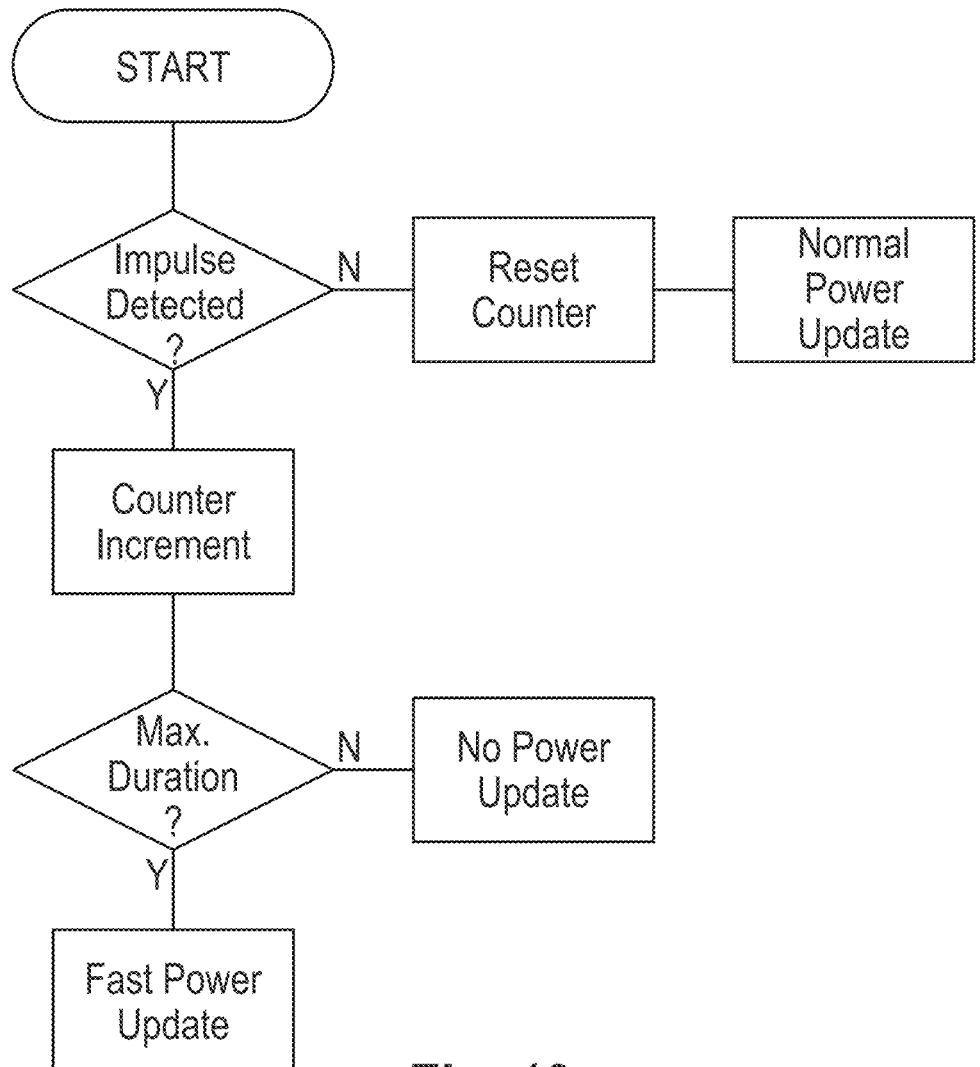
Figure 14A:
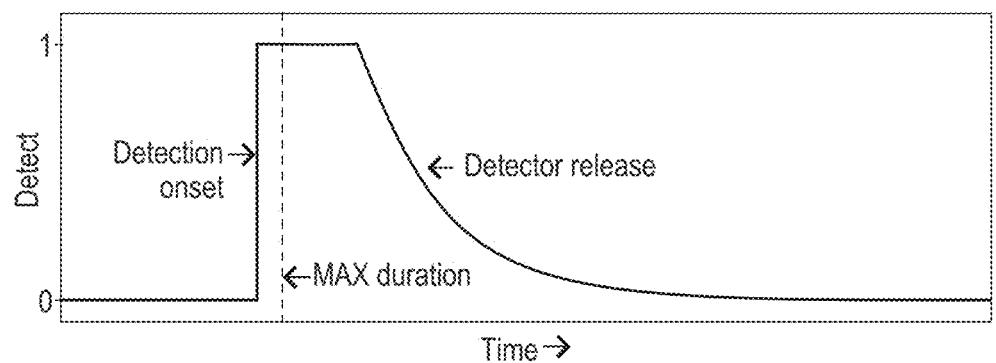
Figure 14B:
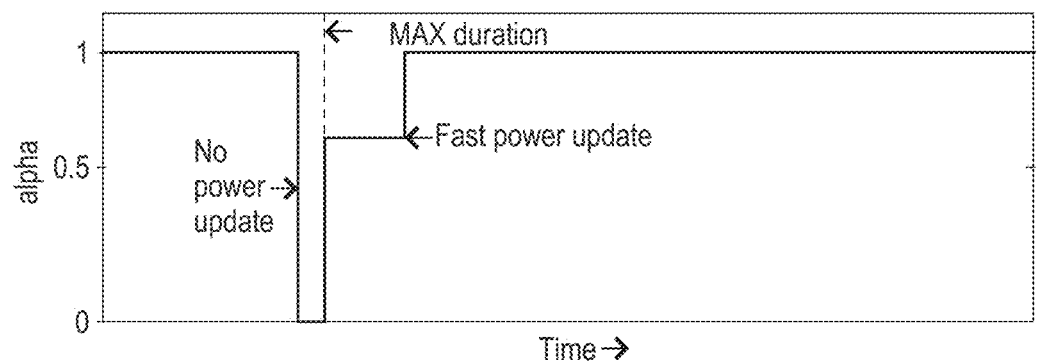
Figure 15:
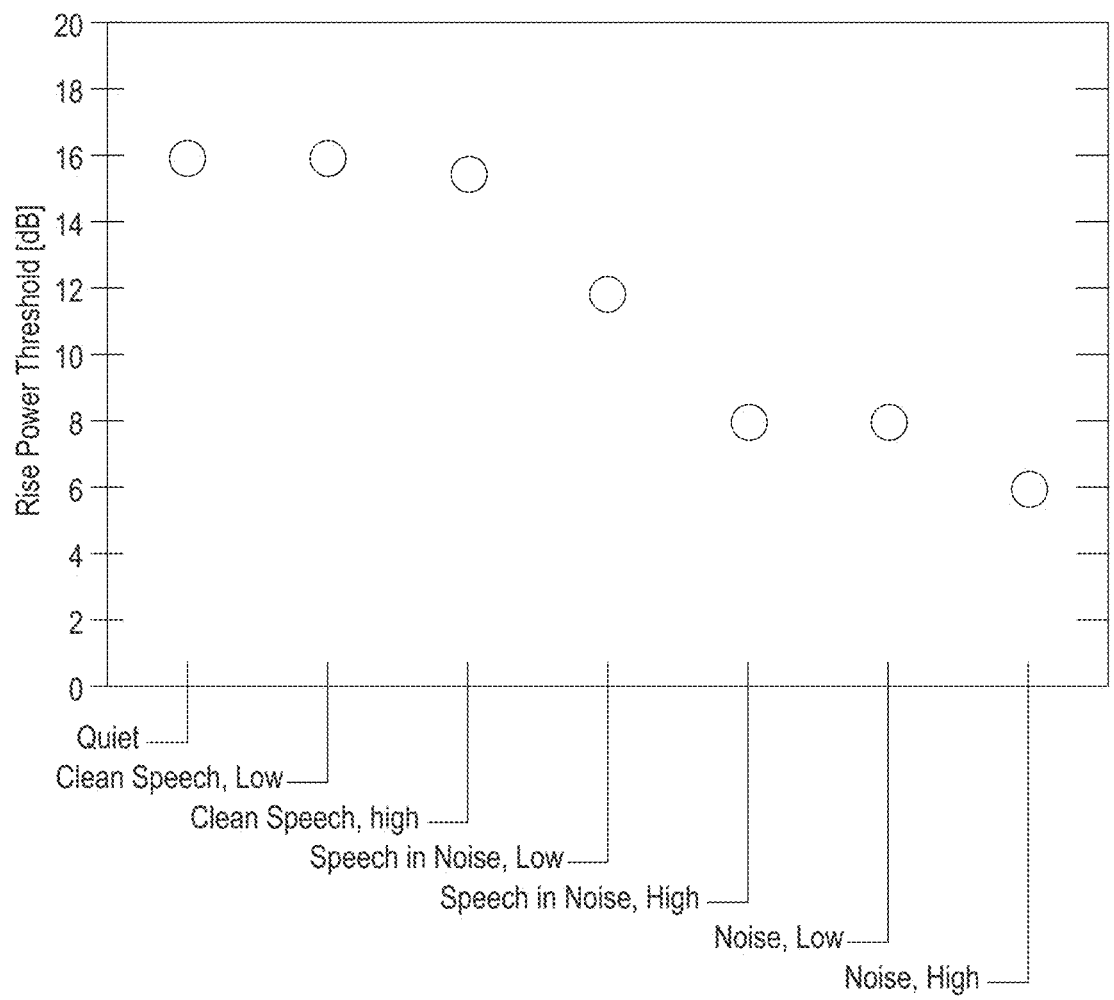
Figure 16:
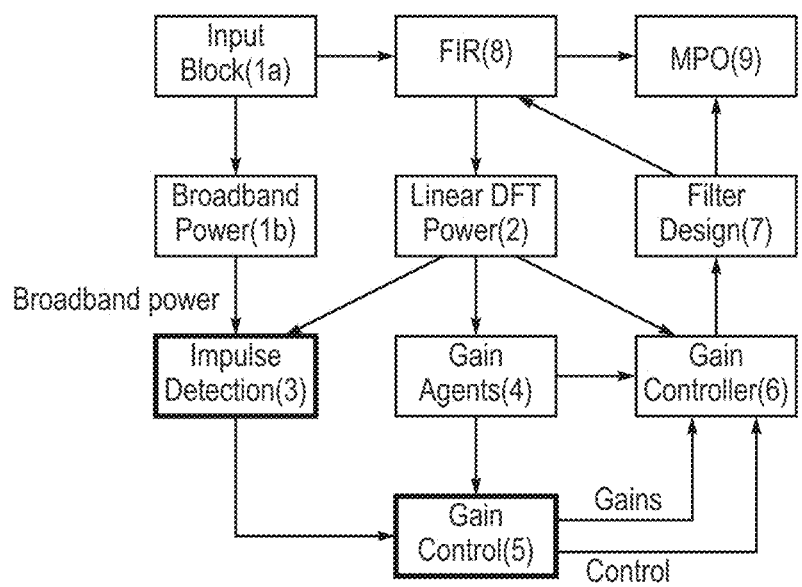

FIG. 6 shows a block diagram of a signal processing scheme of a prior art hearing aid, FIG. 7 shows a plot of delay as a function of frequency in a prior art warped delay line, FIG. 8 shows a block diagram of a signal processing scheme of an embodiment, FIG. 9 shows a plot of warped frequency bands, FIG. 10 shows a plot of frequency bands of an sound impulse detector, FIG. 11 shows a plot of gain reduction as a function of broadband power of an embodiment, FIG. 12 shows plots of impulse detection and gain reduction as a function of time of an embodiment, FIG. 13 shows a flow-chart of power estimation calculation according to an embodiment, FIG. 14 shows plots of impulse detection and α-values as a function of time of an embodiment, FIG. 15 shows a plot of impulse gradient thresholds for different sound environments of an embodiment, and FIG. 16 shows a block diagram of a signal processing scheme of another embodiment.

DETAILED DESCRIPTION OF THE DRAWINGS

Various illustrative examples of the novel hearing device according to the appended claims will now be described more fully hereinafter with reference to the accompanying drawings, in which various embodiments of novel hearing device are illustrated. The novel hearing device according to the appended claims may, however, be embodied in different forms and should not be construed as limited to the embodiments set forth herein. In addition, an illustrated embodiment needs not have all the aspects or advantages shown. An aspect or an advantage described in conjunction with a particular embodiment is not necessarily limited to that embodiment and can be practiced in any other examples even if not so illustrated, or if not so explicitly described.

As used herein, the singular forms "a," "an," and "the" refer to one or more than one, unless the context clearly dictates otherwise.

Figure 1:
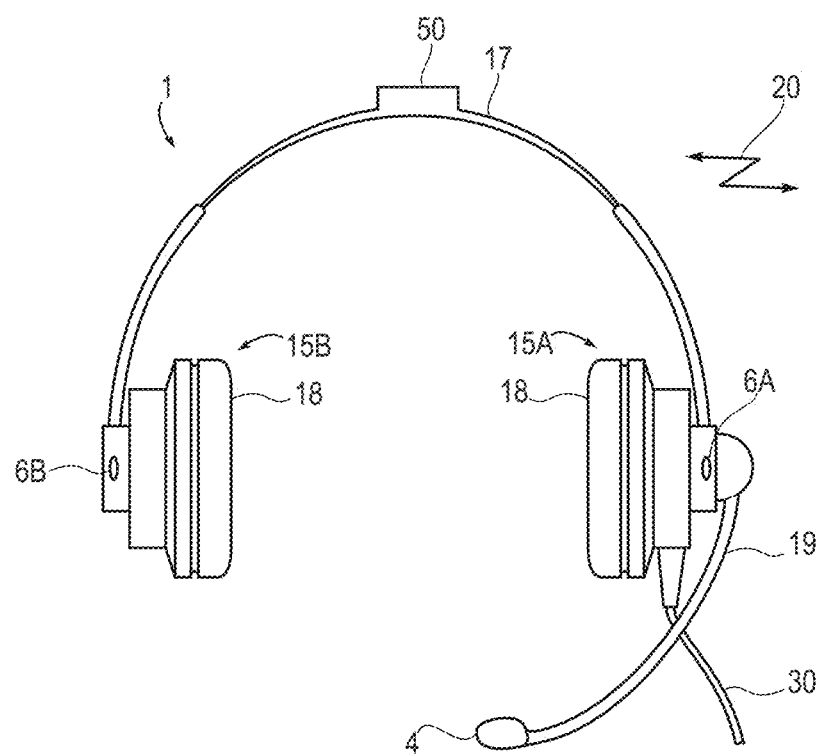

FIG. 1 shows a binaural hearing device system, namely a binaural headset 1 falling under the terms of claim 1 and operating in accordance with claim 15.

The binaural headset 1 has two earphones 15A, 15B interconnected by a headband 17 similar to a conventional corded headset.

Each earphone 15A, 15B of the illustrated headset 1 comprises an ear pad 18 for enhancing the user comfort and blocking out ambient sounds during listening or two-way communication.

A microphone boom 19 with a voice microphone 4 at the free end extends from the first earphone 15A. The microphone 4 is used for picking up the user's voice e.g. during two-way communication via a mobile phone network and/or for reception of user commands.

The housing of the first earphone 15A comprises a first ambient microphone 6A and the housing of the second earphone 15B comprises a second ambient microphone 6B.

The ambient microphones 6A, 6B are provided for picking up ambient sounds and for provision of audio signals in response to the ambient sound. The user can select to mix the audio signals with signals received from another device (not shown), e.g. a mobile phone.

A cord 30 extends from the first earphone 15A to the hand-held device (not shown), e.g. a mobile phone, an IPod®, a GPS-unit, a smart phone, a remote control for the headset 1, etc.

A Bluetooth transceiver of the headset 1 is wirelessly connected by a Bluetooth link 20 to a Bluetooth transceiver in the hand-held device (not shown).

The cord 30 may be used for transmission of audio signals from the microphones 4, 6A, 6B to the hand-held device (not shown), while the Bluetooth network may be used for data transmission of data from the headset 1 to the hand-held device (not shown) and commands from the hand-held device (not shown) to the headset 1, e.g. user commands, such as turn a selected microphone 4, 6A, 6B on or off.

A similar headset 1 may be provided without a Bluetooth transceiver so that the cord 30 is used for both transmission of audio signals and data signals; or, a similar headset 1 may be provided without a cord 30, so that a Bluetooth network is used for both transmissions of audio signals and data signals.

A similar headset 1 may be provided without the microphone boom 19, whereby the microphone 4 is provided in a housing on the cord as is well-known form prior art headsets.

A similar headphone 1 may be provided without the microphone boom 19 and microphone 4.

The user can select to mix ambient sounds picked up by the ambient microphones 6A, 6B with sound received from the hand-held device (not shown).

When mixed-in, sound from the first ambient microphone 6A is directed to the receiver of the first earphone 15A, and sound from the second ambient microphone 6B is directed to the receiver of the second earphone 15B. Thus, the user experiences a spatial effect, whereby the user is able to hear from which direction ambient sounds are coming.

A housing 50 is mounted on or integrated with the headband 17 and interconnected with components in the earphones 15A, 15B through wires running internally in the headband 17 between the housing 50 and the earphones 15A, 15B.

Figure 5:
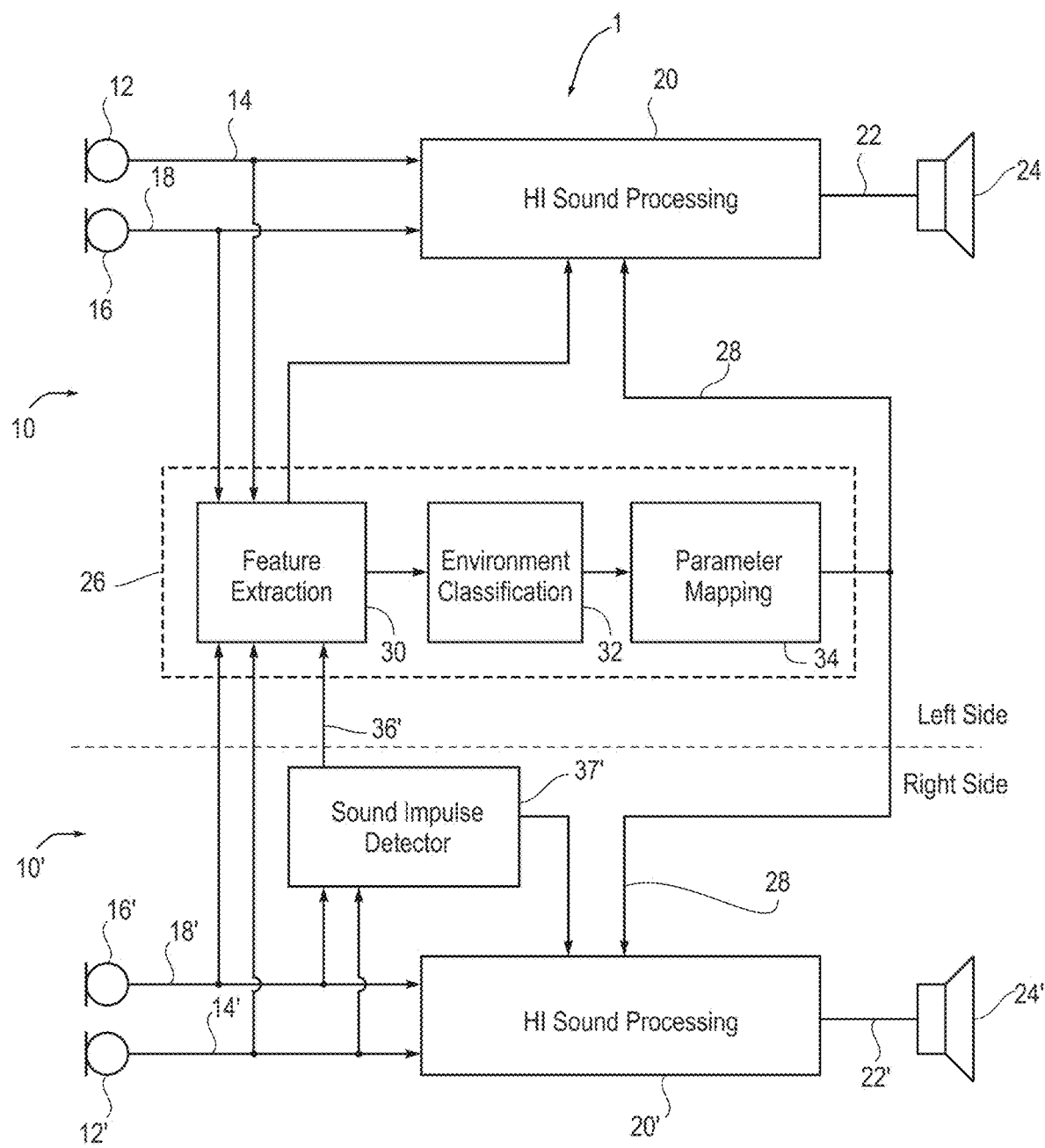

The housing 50 accommodates signal processing circuitry of the headset 1 that is identical to the circuitry illustrated in FIG. 5 except for the fact that no hearing loss compensation is provided by the headset 1 and no signal processing circuits are accommodated in the earphones 15A, 15B, and each of the earphones 15A, 15B accommodates a single respective ambient microphone 12, 12' (not visible in FIG. 1), and the respective receiver 24, 24' (not visible in FIG. 1). All electrical interconnections shown in FIG. 5 are provided as wired interconnections in the headset 1.

The user interface of the headset 1 is not visible, but may include one or more push buttons, and/or one or more dials as is well-known from conventional headsets in addition to a user interface provided by the hand-held device (not shown).

Figure 2:
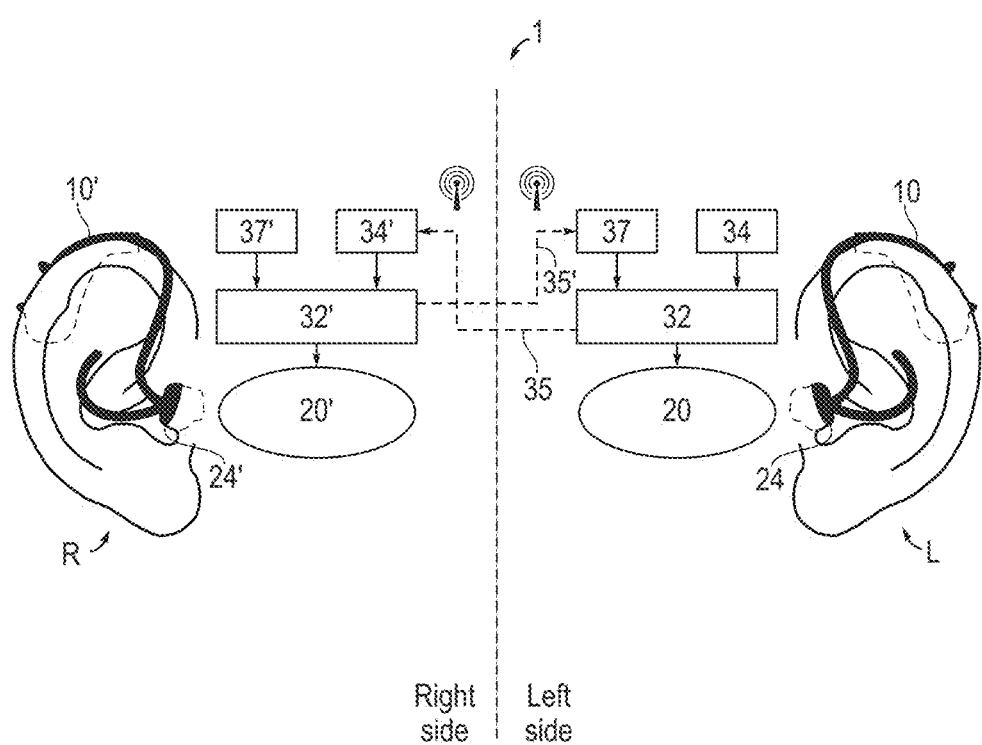

FIG. 2 illustrates a binaural hearing device system, namely a binaural hearing aid system 1, falling under the terms of claim 1 and operating in accordance with claim 15. The binaural hearing aid system 1 comprises a first hearing aid 10 that is adapted to provide compensation of hearing loss of a left ear L of a user and a second hearing aid 10' that is adapted to provide compensation of hearing loss of a right ear R of a user. A first hearing loss compensated audio signal is provided by the first hearing aid 10 via a first output receiver 24 to the left ear L of the user, and a second hearing loss compensated audio signal is provided by the second hearing aid 10' via a second output receiver 24' to the right ear R of the user.

Next to the first ear L is shown a block diagram of a first impulse suppression algorithm comprising a first sound impulse detector 34, a first external impulse detection block 37, a first binaural impulse environment detector 32 and a first sound processing optimization block 20. Likewise, next to the second ear R is shown a block diagram of a second impulse suppression algorithm comprising a second sound impulse detector 34', a second external impulse detection block 37', a second binaural impulse environment detector 32' and a second sound processing optimization block 20'.

During use, the first binaural impulse environment detector 32 provides information about its operational modus to the second impulse detection block 37' via a wireless connection 35, and the second binaural impulse environment detector 32' provides information about its operational modus to the first impulse detection block 37 via a wireless connection 35'.

Thus, the first hearing aid 10 and the second hearing aid 10' of the hearing aid system 1 are capable of mutually exchanging information regarding impulse environment conditions via the wireless connections 35 and 35'. If both hearing aids 10, 10' detect that they are in an impulse environment, their modus of operation may change in order to reflect this condition. If only the first hearing aid 10 detects that it is in an impulse environment, it provides this information from its binaural impulse environment detector 32 to the impulse detection block 37 of the second hearing aid 10' via the wireless connection 35. However, since the second hearing aid 10' is not detecting an impulse environment, it may choose to continue to operate normally, i.e. as if no impulse were detected. If the second hearing aid 10' detects an impulse environment itself, it is, however, prepared to take action faster and change to an impulse suppression operational modus.

Figure 3:
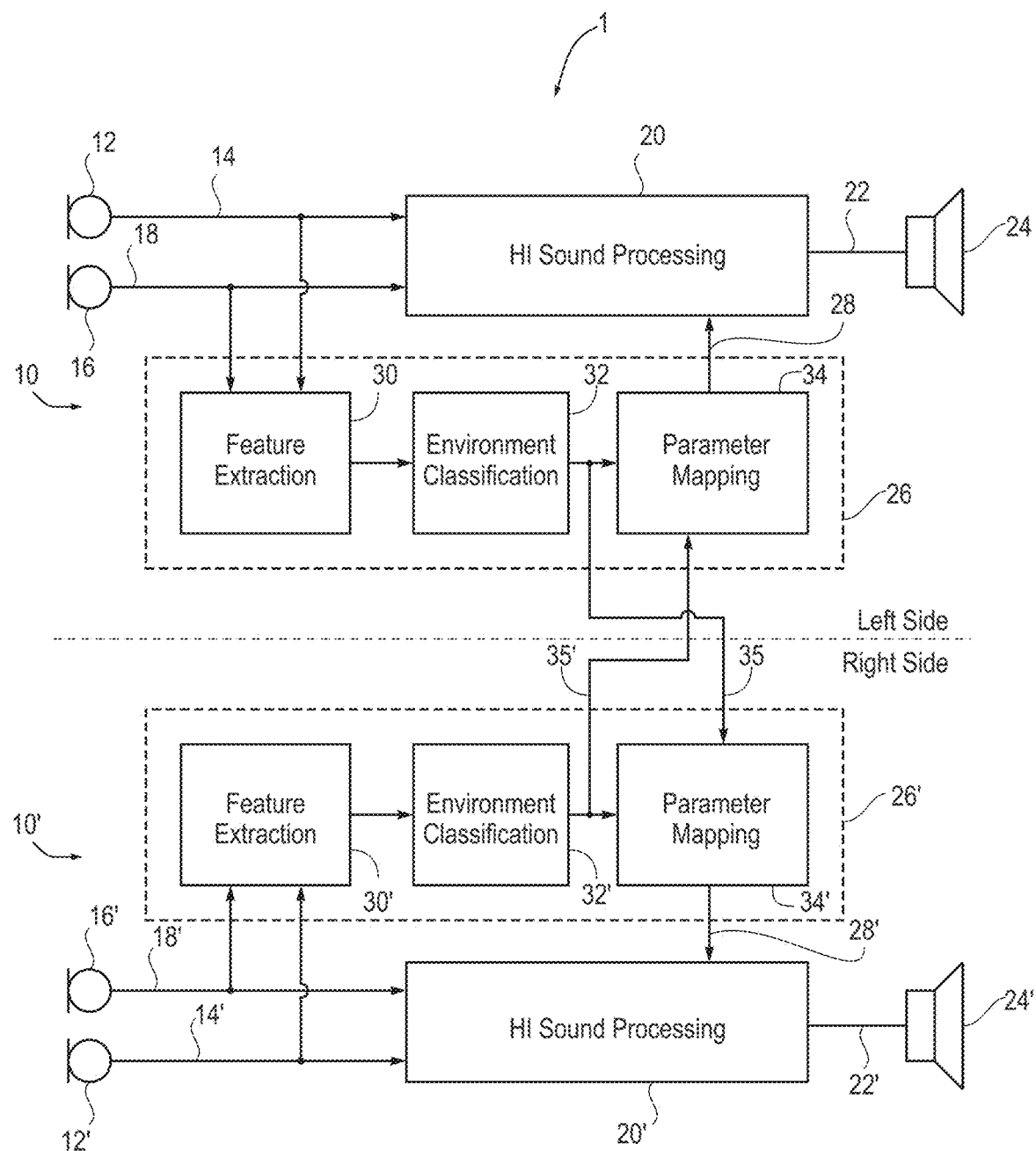

FIG. 3 is a block diagram of a binaural hearing device system, namely a binaural hearing aid system 1, falling under the terms of claim 1 and operating in accordance with claim 15.

The binaural hearing aid system 1 comprises a binaural hearing aid with a first hearing aid 10 that is adapted to provide compensation of hearing loss of the left ear of a user and a second hearing aid 10' that is adapted to provide compensation of hearing loss of the right ear of a user.

Each of the first hearing aid 10 and second hearing aid 10' comprises a front microphone 12, 12' and a front A/D converter (not shown) for provision of a digital input signal 14, 14' in response to sound signals received at the first front microphone 12, 12' in a sound environment, and a first rear microphone 16, 16' and a rear A/D converter (not shown) for provision of a digital input signal 18, 18' in response to sound signals received at the rear microphone 16, 16', a signal processor 20, 20' that is adapted to process the digital input signals 14, 14', 18, 18' in accordance with a predetermined signal processing algorithm to generate a processed output signal 22, 22', and a D/A converter (not shown) and an output receiver 24, 24' for conversion of the processed sound signal 22, 22' to an acoustic output signal for emission towards the left and right eardrums, respectively, of the user.

Each of the hearing aids 10, 10' further comprises a binaural sound environment detector 26, 26' for determination of the sound environment surrounding a user of the binaural hearing aid 1. The determination is based on the audio signals 14, 18, 14', 18' provided by the respective front and rear microphones 12, 16, 12', 16' of both hearing aids, i.e. binaurally, whereby the signal processors 20, 20' is automatically switched in co-ordination to the most suitable algorithm for the determined environment whereby optimum sound quality and/or speech intelligibility is maintained in various sound environments by the binaural hearing aid system 1.

Based on the determination, each of the binaural sound environment detectors 26, 26' provides outputs 28, 28' to the respective signal processor 20, 20' for selection of the signal processing algorithm appropriate in the determined sound environment for execution by the respective signal processor 20, 20'. Thus, each of the signal processors 20, 20' is automatically switched to the most suitable algorithm for the determined environment whereby optimum sound quality and/or speech intelligibility is maintained in various sound environments.

Each of the binaural sound environment detectors 26, 26' comprises a respective feature extractor 30, 30' for determination of characteristic parameters of the respective audio signals 14, 18, 14', 18'.

Each of the feature extractors 30, 30' maps the respective audio signals 14, 18, 14', 18' into sound features, i.e. the characteristic parameters. These features may include signal power, spectral data and other well-known features.

Each of the binaural sound environment detectors 26, 26' further comprises an environment classifier 32, 32' for categorizing the sound environment based on the determined characteristic parameters.

Each of the environment classifiers 32, 32' categorizes the sounds into a variety of environmental classes, including speech, babble speech, music, traffic noise, impulse environment, such as restaurant clatter, etc. The classification process may consist of a simple nearest neighbour search, a neural network, a Hidden Markov Model system or another system capable of pattern recognition. The output of the environmental classifier can be a "hard" classification containing one single environmental class or a set of probabilities indicating the probabilities of the sound belonging to the respective classes. Other outputs may also be applicable.

Each of the binaural sound environment detectors 26, 26' further comprises a respective parameter map 34, 34' for the provision of respective outputs 28, 28' for selection of the signal processing algorithms for execution in the respective signal processor 20, 20'.

Each of the parameter maps 34, 34' maps the output of the environment classifiers 32, 32' to a set of parameters for the respective signal processor 20, 20'. Examples of such parameters are amount of noise reduction, amount of gain and amount of HF gain. Other parameters may be included.

Signals are transmitted between the first and second hearing aids 10, 10' so that the signal processing algorithms executed by the signal processors 20, 20' are selected in co-ordination, e.g. in case of an omni-directional sound environment, i.e. the sound environment does not change with direction, the signal processing algorithms are selected to be identical apart from differences caused by possible differences in hearing loss compensation provided to the respective ears.

The output 38, 38' of the environment classifier 32, 32' of one hearing aid 10, 10' is transmitted to the respective other parameter mapping 34, 34' of the respective other hearing aid 10', 10 via wireless connections 35, 35'. The parameter map 34, 34' then operates on two inputs 38, 38' to produce the parameters for the signal processing algorithms, but since both parameter mapping units 34, 34' receive identical inputs, identical parameter values will be produced apart from differences caused by possible differences in hearing loss compensation provided to the respective ears.

In this way, the transmission data rate over the connections 35, 35' is low, since only a set of probabilities or logic values for the environment classes has to be transmitted.

Also, rather high latency can be accepted. By applying time constants to the variables that will change according to the output of the parameter mapping, differences caused by latency are low-pass filtered. If transition periods of a few seconds are allowed the binaural hearing aid system can operate with only 3-4 transmissions per second via the connections 35, 35'.

Hereby, power consumption is kept low.

Each of the feature extractors 30, 30' comprises a respective sound impulse detector that is adapted for detecting presence of an impulse in the respective audio signals 14, 18, 14', 18' and outputting an impulse detected signal indicating when an impulse is detected as explained in more detail below with reference to FIGS. 8-16.

The impulse detected signal is provided to the respective environment classifier 32, 32' so that an impulse environment can be determined by the environment classifier 32, 32' and so that the respective parameter map 34, 34' can provide respective outputs 28, 28' for selection of the proper signal processing algorithms for execution in the respective signal processor 20, 20' in response to determination of an impulse environment at both ears of the user. Thus, the binaural impulse environment detector is duplicated so that each of the binaural sound environment detectors 26, 26' comprises one binaural impulse environment detector.

Each of the signal processors 20, 20' comprises a respective sound impulse suppressor that is adapted for attenuating the impulse by signal processing parameter adjustment, e.g. by gain adjustment, attack time adjustment, release time adjustment, etc., in response to the respective outputs 28, 28' of the parameter maps 34, 34'.

For example, in a sound environment without sound impulses, the signal processors 20, 20' of the first and second hearing aids 10, 10' may operate in accordance with a signal processing algorithm wherein each of the sound impulse suppressors operates monaurally, i.e. independent of sound received at the other ear of the user, for fast, preferably instantaneous, suppression of sound impulses in the respective audio signals 14, 18, 14', 18' in response to impulse detection by the respective sound impulse detector as explained in more detail below with reference to FIGS. 8-16, until the binaural impulse environment detectors included in the respective binaural sound environment detectors 26, 26' determine that the sound environment has changed to an impulse environment and control the signal processors 20, 20' to operate in accordance with a signal processing algorithm for optimum signal processing in the impulse environment, e.g. for example controlling the sound impulse suppressors to lower the resulting gain of the signal processors 20, 20' by the same amount to avoid distortion of spatial cues contained in the processed audio signals 22, 22', whereby the user can maintain sense of direction.

The first and second hearing aids 10, 10' are interconnected in a Bluetooth LE wireless network for transmission of the output signals 35, 35' of the environment classifiers 32, 32' to the respective one of the first and second hearing aids 10, 10'.

Figure 4:
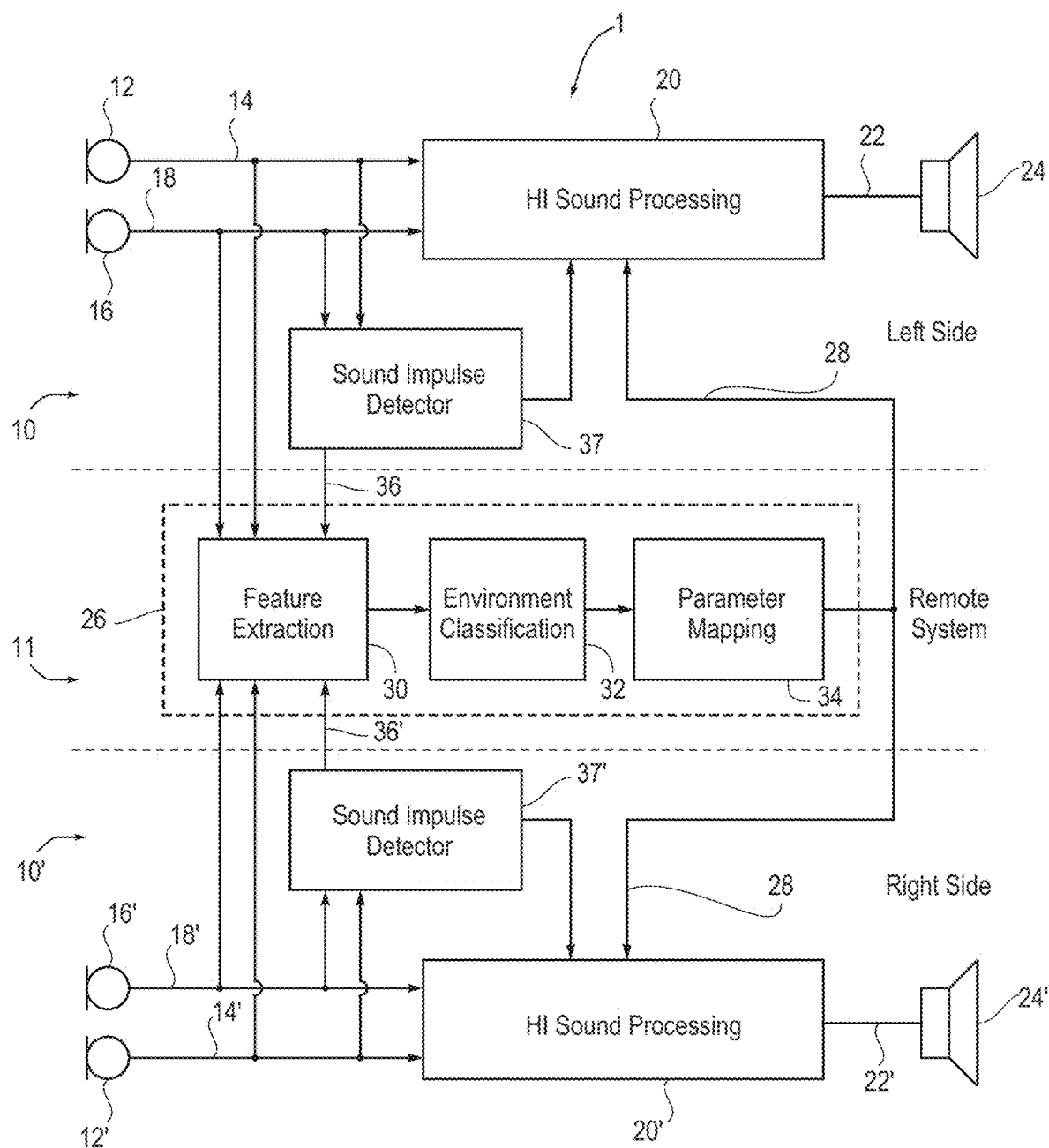

FIG. 4 is a block diagram of another binaural hearing aid system 1 falling under the terms of claim 1 and operating in accordance with claim 15.

The binaural hearing aid system 1 comprises a first hearing aid 10 that is adapted to provide compensation of hearing loss of the left ear of a user and a second hearing aid 10' that is adapted to provide compensation of hearing loss of the right ear of a user and a smartphone 11 comprising the binaural environment detector 26 including the binaural impulse environment detector of the system.

The circuitry of the first and second hearing aids 10, 10' is identical to the circuitry of the first and second hearing aids 10, 10' shown in FIG. 3 except for the fact that the binaural sound environment detectors 26, 26' of the first and second hearing aids 10, 10' shown in FIG. 3 have been combined and moved to the smartphone 11 in FIG. 4 so that, in FIG. 4, the determination of the sound environment is performed by a single binaural sound environment detector 26 based on the audio signals 14, 18, 14', 18' and the impulse detected signals 36, 36' provided by sound impulse detectors 37, 37' of both hearing aids 10, 10'.

The smartphone 11 and the first and second hearing aids 10, 10' are interconnected in a Bluetooth LE wireless network for transmission of the audio signals 14, 18, 14', 18' from the first and second hearing aids 10, 10' to the smartphone 11 and for transmission of the output signal 28 of the binaural sound environment detector 26 to the first and second hearing aids 10, 10'.

FIG. 5 is a block diagram of yet another binaural hearing aid system 1 falling under the terms of claim 1 and operating in accordance with claim 15.

The binaural hearing aid system 1 comprises a first hearing aid 10 that is adapted to provide compensation of hearing loss of the left ear of a user and a second hearing aid 10' that is adapted to provide compensation of hearing loss of the right ear of a user.

The circuitry of the first and second hearing aids 10, 10' is identical to the circuitry of the first and second hearing aids 10, 10' shown in FIG. 3 except for the fact that the binaural sound environment detectors 26, 26' including respective binaural impulse environment detectors of the first and second hearing aids 10, 10' shown in FIG. 3 have been combined in the binaural sound environment detector 26 including one binaural impulse environment detector of the first hearing aid 10 in FIG. 5 so that, in FIG. 5, the determination of the sound environment is performed by a single binaural sound environment detector 26 with a single binaural impulse environment detector based on the audio signals 14, 18, 14', 18' of both hearing aids 10, 10' and the impulse detected signal 36' from the sound impulse detector block 37' of the second hearing aid 10'.

The first and second hearing aids 10, 10' are interconnected in a Bluetooth LE wireless network for transmission of audio signals 14', 18' of the second hearing aid 10' to the first hearing aid 10 and of the output signal of the binaural sound environment detector 26 to the second hearing aid 10'.

FIG. 6 schematically illustrates a prior art hearing aid signal processing scheme 10 with dynamic signal compression performed in a hearing aid compressor well-known in the art of hearing aids.

The known hearing aid compressor performs a warped frequency transformation and controls the gain in 17 warped frequency bands corresponding to the Bark frequency scale of human hearing. The gains are controlled in accordance with the fitting rule of the hearing aid and the hearing loss of the user of the hearing aid so that the dynamic range of a human with normal hearing is compressed into the residual dynamic range of the user with a hearing loss resulting in loss of dynamic range as is well-known in the art of hearing aids. The attack and release time constants are quite long in order to avoid distortion of speech.

The trade-off is that short, intense sounds might be over-amplified and in combination with the rapid increase in perceived loudness, also known as recruitment, this could potentially be a downside of the hearing aid compressor.

Due to the nature of sound impulses, such as door slamming, clinking of silverware, jangling of keys, etc., hearing aid users are often left with discomfort and annoyance in their daily usage.

In many cases a very rare occurring event, influences the hearing device usage in such a way, that the hearing impaired user might lose all the intended benefits from wearing the devices. Turning down the volume or slightly removing the hearing device from the ear, which, to some extent, is similar to a frequency dependent gain reduction, is something that an algorithm should be able to do both faster and more effective. In order to obtain suitable impulse suppression, impulse detection and response have to be performed with minimum delay, e.g. maintaining un-assisted loudness during the impulse.

For mild hearing losses, protecting against sound impulses could also have another effect; preserving hearing. Persons with normal hearing have what is sometimes referred to as the acoustic reflex which is initiated by high sound pressure levels (SPL). It selectively reduces the intensity of sound transmitted to the inner ear; however with a short delay of approximately 20 ms originating from the intrinsic reaction time of the stapedius and the tensor tympani muscles. Hence, high level impulse sounds such as gun shots may be too short for the muscles to react to, resulting in possibly permanent hearing loss.

Hearing device users with certain combinations of hearing loss and configurations are also disturbed more by less intensive soft sound impulses. This could be the clicking of a computer's keyboard, or rustling paper.

The novel sound impulse detector and/or sound impulse suppressor may be adjustable in accordance with user inputs.

In the illustrated embodiment, gain adjustments are performed taking the current gain settings of the hearing aid compressor into account.

The known warped hearing aid compressor signal processing scheme is illustrated in a high level in FIG. 6. The numbering indicates the order of execution within one block of samples. The delay from input to output of the compressor is equal to the time of sampling one block of samples, e.g. a few milliseconds.

Estimating power with critical band resolution is achieved by warping the delay line. A set of all-pass filters serve to implement frequency-dependent unit delays, low frequencies are stretched and high frequencies are compressed. The group-delay as illustrated in FIG. 7, for a high bandwidth configuration, is low at high frequencies while the low frequency area is exposed to a longer group delay. It can be observed that for a compressor system based on the state remaining from the last input sample in each block, the group-delay at high frequencies is much lower than the block rate ~1.5 ms.

In other words, there is a risk that a sound impulse detector based on the warped delay-line potentially underestimates the high frequency part of blocks with an impulse. High bandwidth platforms have a slightly different implementation of the Maximum Power Output (MPO) block that is adapted for limitation of the output power of the hearing device, compared to the normal bandwidth platforms. The MPO has been updated to avoid sudden changes in the static gain operation. A high bandwidth MPO partially applies the static gain changes in intervals of two samples; the full gain change is applied within one block of samples. An impulse gain reduction build on top of the existing MPO, would further imply a change in order to deal with the gain update-delay in the direct sound path.

In order to be able to attenuate impulses, a sound impulse detector is added to the dynamic hearing aid compressor.

The signal processing scheme of a combined sound impulse detector, gain adjustment, and dynamic hearing aid compressor is shown in FIG. 8.

Comparing the execution order of the submodules to the execution order shown in FIG. 6 indicates that the Gain controller and Filter Design are now executed before the direct path processing. The Warp Power is still based on the previous blocks and all gain agents are still processing the same data as before i.e. the dynamic hearing aid compressor is not changed. A novel Gain Calculation block has been added before the Gain controller, and an instant change of frequency response can be obtained. If the sound impulse detector and the Gain Calculation block are disabled, the illustrated processing scheme will be identical to the processing scheme shown in FIG. 6, i.e. the processing scheme of the known dynamic hearing aid compressor.

Detecting sound impulses in the frequency domain is performed utilizing a second frequency domain transformation. Addressing complexity, resolution and flexibility, the linear DFT in equation (1) is the starting point for the sound impulse detector.

$$X[n] = \sum_{k=0}^{N-1} x(k) e^{-j\frac{2\pi}{N}nk} \qquad (1)$$

Preferably, the sound impulse detector should work on the unprocessed input block. This is illustrated in FIG. 8, where (2) indicates frequency domain transformation, following the new arrived input block of audio samples. Particularly it is of interest how the power rises over time, when looking for impulse patterns. Equation (2) shows the frequency domain power estimate P[n] of the current block.

$$P[n] = \text{abs } (X[n])^2 \qquad (2)$$

Input blocks of samples, that exhibit impulsive nature must have an approximately instant rise time. In addition, the impulsive characteristic causes a power distribution that spans many bands. A smoothed version of the power estimates per bands $\tilde{P}[n]$ is used for the instant rise feature extraction. The parameter $\alpha$ in equation (3) should be chosen sufficiently small, in order to explore the instant rise time of the impulse relative to a short history of background power.

$$\tilde{P}[n]=P[n](1-\alpha)+\alpha\tilde{P}[n] \quad (3)$$

For an optimized performance during repetitive impulses, the smoothed power estimates is not allowed to be updated during detected impulses. In addition, the ability to efficiently track the impulse relies on the possibility to compare the frequency domain power of the impulse with the energy just before the impulse onset. Dividing the current power estimate with the smoothed version as in equation (4), can be used as a measure of how much the power in the different bands has raised with the new block of samples.

$$r(n) = \frac{P[n]}{\tilde{P}[n]} \quad (4)$$

For implementation complexity reasons, the rise measure r(n), could advantageously be implemented in the $\log_2$ domain. The precision of the $\log_2$ is found to be accurate enough, and the remaining part of the sound impulse detector could improve by having decision and threshold implemented in the logarithmic domain, equation (5).

$$r(n)=\log_2(P[n])-\log_2(\tilde{P}[n]) \quad (5)$$

It could be argued that, due to the window size, the power estimates are poor for the lowest bands. For simplicity and in order to align with the existing hearing device platform the number of bands L is defined as equation (6)

$$L = \frac{N}{2} + 1 \quad (6)$$

where N is the size of the DFT and accordingly, in a non-overlap implementation, is equal to the processing block-size. Now, a vector $r_t$ builds of L bands rise measures in the $\log_2$ domain can be constructed $$r_t=[r(0),r(1),\ldots,r(L-1)] \quad (7)$$

wherein t is block rate which for a high bandwidth hearing device platform is $$T_{block} = N \cdot \frac{1}{fs} \approx 1.5 \text{ ms} \quad (8)$$

In effect the block rate in eq. (8) also sets the lower limit of the impulse rise time that the sound impulse detector can observe. Keeping in mind that this limit is not to be confused with the scheme in FIG. 8, which can apply gain reduction instantly with no delay from the detection point. One major point of concern for a sound impulse detector will always be whether it distinguishes between impulse sounds like door slamming, cutlery etc. and speech onset, which is the portion of vocalization where impulse-like characteristics can be ascertained. One way of addressing this issue could be to include a threshold that would operate on the vector $r_t$. Now eq. (9) defines a measure of how many bands in the present power estimate exceeds this threshold.

$$R_t=\text{sum}(r_t>\text{RiseThreshold}) \quad (9)$$

The threshold in eq. (9) would be defined in the $\log_2$ domain. Impulse noises that are annoying in nature for hearing device users typically have a broad power spectrum spanning a large number of frequency bands, which is not the case for speech. Defining that the sum of power bands with instant rise time $R_t$ should be above, e.g. 10, assists in distinguishing impulse noise from speech in the sound impulse detector. At this point a true/false parameter of impulse detection is available.

A final broadband power threshold is also applied to ensure that only impulsive blocks above a particular sound-pressure level are detected. This threshold is applied in order to configure the sensitivity of the sound impulse detector. For end-users that only find intense impulses like door slams annoying, this threshold can be increased compared to users who are disturbed by more weak impulses, defined like the clicking of a computer keyboard, clattering dishes etc. For example firecrackers can reach level as high as 180 $dB_{SPL}$.

A broadband power threshold of the sound impulse detector has a naturally lower limit as indicated in table 1 above.

In order to apply even more robustness towards knowing the difference between speech onset and targeted impulse sounds, this threshold must be set high enough to operate on top of the normal speech production area. The pseudo code in Algorithm 1:

If $R_t \geq 10$ then
    detect = 1
else
    detect = $\alpha_{detect}$ · detect
end if
if detect = 0 then
    for n=0:Nbands−1 do
        $\tilde{P}[n] = P[n](1 - \alpha_{smooth}) + \alpha_{smooth} \tilde{P}[n]$
    end for
end if summarizes impulse detection of the sound impulse detector. The output parameter of the detection algorithm is detect, which holds values between zero and one (0≤detect≤1). For detect to reach zero after an impulse has decayed to a state where it is no longer exploring impulsive characteristics, or does not longer comply with the broadband power threshold, a logarithmic release time is applied. The parameter $\alpha_{detect}$ is used to specify the release time, while the attack time of detect is instant.

A frequency-warped FIR filter can be designed by replacing the unit delays in the conventional FIR filter with all-pass filter sections. It serves to match the frequency resolution of the compression system to the resolution of the human auditory system. Additionally the warped filter has a higher group-delay at low frequencies than a conventional filter for the same low frequency resolution. As discussed earlier, the short delay at high frequencies is problematic for a sound impulse detector e.g. under-sampling can lead to false detection. In addition, the frequency resolution of a DFT based on a warped delay line can limit the performance of the detection scheme as well. The warp Compressor system, or more important the power estimator, is based on the warped delay line utilizing the all-pass transfer function in equation 10.

$$H(z) = \frac{a+z^{-1}}{1+az^{-1}} \quad (10)$$

where a is the warping parameter. Combined with the warp window this leads to the 17 bands illustrated in FIG. 9. The warped frequency scale gives a much better match to auditory perception compared to a linear based system. However, serving to detect and differentiate impulse noises from the daily sound environment including own and surrounding speech, the warp-based DFT delivers poor performance. In order to use the number of frequency bins with instant power rise as a feature for detecting impulsive input blocks, a much better resolution is needed in the highest bins. In addition the warp window is constructed to smear adjacent bins to avoid drastic gain differences by the filter designer. The sound impulse detector utilizes a 32-point linear FFT with a Tukey window. FIG. 10 illustrates the frequency resolution of the 17 bands. This configuration will not favour speech-like signals. Another choice could be to use a warped delay line with a positive warping factor. This would further increase the resolution of the highest bins, leading to a detection even more focused on instant power increase in regions not dominated by speech. The primary disadvantage of a detection scheme based on a parallel warped delay line is the computational cost of replacing unit delays with first-order all-pass filters.

The DFT implicit assumes that the signal is periodic in the time frame. When the input block is not periodic then leakage occurs. Leakage results in misleading information about the spectral amplitude and frequency. For the sound impulse detector, the worse impact is leakage to adjacent bins, which might lead to false detection. The sound impulse detector relies on identification of bands with rapid increase of sound power; spectral leakage contributes to the risk of false detection. A DFT window can be applied to reduce the effects of leakage.

$$\dot{x}(n) = x(n)w(n) \quad (11)$$

$$\dot{x}_t = [\dot{x}(0), \dot{x}(1), \ldots, \dot{x}(N+1)] \quad (12)$$

$$X_t = DFT(\dot{x}_t) \quad (13)$$

The Gain calculation block may reduce broad-band gain, e.g. the gain in all of the frequency bands, in a plurality of the frequency bands, such as in more than half of the frequency bands, of the compressor in order to attenuate the impulse.

The Gain calculation block may restore natural loudness of signals like slamming doors, clinking of silverware or jangling of keys, in response to impulse detection. These are all examples of sounds that are part of the daily sound environment, but in most cases will generate an unnatural and painful representation at the ear-drum of the hearing device user. Focusing on the end-user and what causes the discomfort, the Gain Calculation block must be able to address the over-amplification of short duration impulsive signals. Most likely the unnatural reproduced segments are caused by the linear part of the prescribed gain i.e. the $G_{50}$ gain is applied for high energy impulse signals. In other words, what causes the discomfort is end-user dependent and most likely described by the $G_{50}$ gains. This also means that the sound impulse suppressor needs to control gain independently in the 17 frequency bands, in order to match the behaviour of the warp system.

The sound impulse suppressor is adapted for attenuating the impulse to a comfort level still being descriptive of the acoustic environment. A very simple approach that does not add significant complexity to the run-time part of the algorithm could be to utilize a gain look-up table. A look-up table would map the broadband power of an impulse section, to a reduction vector, with the needed gains for the 17 warped bands. A given fitting rule is used to reach the prescribed gain based on the hearing threshold. In a two power bands configuration, the prescribed gain is implemented by the target $G_{50}$ and $G_{80}$ gains. Define a broadband power threshold vector B as a starting point $$B = [b(0), b(1), \ldots, b(P-1)] \quad (14)$$

where P is the power table size i.e. the resolution of the steps that can be achieved. The span of power, or the SPL area that sound impulse suppressor should work within is defined as $$\text{power\_span} = B[P-1] - B[0] \quad (15)$$

The target gains are now mapped linearly into this area by means of the parameters min reduction and max reduction. Where min reduction in dB defines the reduction at the lower boundary of the B vector and max reduction defines the reduction at the top of the vector. E.g. it is defined how much of the target gains, $G_{50}$, that the sound impulse suppressor will correct for at a given SPL. Use the relative distribution of broadband power level thresholds AR in order to normalize this vector $$\hat{B} = \left[ 0 \, cumsum\left(\frac{\Delta B}{\text{power\_span}}\right) \right] \quad (16)$$

The normalized vector $\hat{B}$ can be used to linearly interpolate from the two-dimensional space defined by min reduction and max reduction, into the dimension of the B vector. The outcome is a vector with gain reduction ratios, in dB, per broadband power level. These reduction numbers are relative to the $G_{50}$ target gains and the final the sound impulse suppressor gains are now defined as a P by 17 matrix G. If min reduction is set to 6 dB, the sound impulse suppressor will apply half of the target gain in reduction during an impulse with the lowest broadband power. This will then linearly increase up to e.g. max reduction set to 0 dB, where the sound impulse suppressor will reduce the gains equal to the target gains i.e. fully compensate for the AGCI (Automatic Gain Control-Input) gains. FIG. 11 illustrates how the target $G_{50}$ gains are mapped to the sound impulse suppressor gain reductions. This example has the broadband power threshold vector B set to $$B = [86\ 90\ 94\ 96\ 100\ 110][dBSPL] \quad (17)$$

and the target $G_{50}$ gains used was $$G_{50} = [7\ 7\ 7\ 7\ 7\ 7\ 7\ 9\ 10\ 11\ 12\ 14\ 16\ 18\ 26\ 33\ 34]\ [dB] \quad (18)$$

With min reduction set to 6 dB and max reduction set to 0 dB, it is observed how the gain reduction gradually increases from half the $G_{50}$ target gains, at an impulse broadband power of 86 dB SPL, up to full compensation at 110 dB SPL. When maximum broadband power is reached in the B vector, the sound impulse suppressor gain reduction is locked to this level. In addition, the broadband power threshold used in the detection part should be the same value as the first entry of the B vector. This will align the sound impulse detector and the gain calculation block with respect to active area of operation.

In the attempt of securing listening comfort for a broad representation of hearing threshold fittings, the ability of adjusting the sensitivity of the sound impulse detector is needed. Users might express special needs and annoyance levels, e.g. some hearing impaired might feel discomfort even for less intensive impulse-like sounds like clicking of a computer's keyboard, rustling paper etc. There might also be a need for different sensitivity in order to address acclimatization for first-time hearing device users. A simple mild, medium and strong approach is preferred. This can be achieved by addressing the broadband power levels during impulses differently, i.e. by defining the vector B per mode. An example of how the sound impulse detector modes could be adapted is shown in table 2 listing sound impulse detector modes (mild, medium, strong) aligned with broadband power thresholds dB SPL.

TABLE 2

| | low | | ... | | | high |
|---|---|---|---|---|---|---|
| Mild | 90 | 94 | 98 | 100 | 104 | 114 |
| Medium | 86 | 90 | 94 | 96 | 100 | 110 |
| Strong | 75 | 78 | 80 | 84 | 86 | 90 |

In combination with the B vector being set per mode, max reduction and min reduction could also be included. This enables the sound impulse detector and sound impulse suppressor to define modes by means of the levels of where to reduce gains, and indeed also how much to reduce gain.

When dealing with discomfort, by reducing gain during impulse sounds, the sound impulse suppressor applies the smallest attack time achievable. This is possible as already observed in the re-arranged warp system in FIG. 8. The broadband power is expected to vary during an impulse; the impact could be that the gain reduction applied will fluctuate causing distortion. This potential issue increases with more extreme settings of the modes in table 2, e.g. if a mode spans a large area of sound pressure levels. A way of addressing fluctuating sound impulse suppressor gains could be to apply an impulse onset detection parameter. In FIG. 12A this is illustrated. An impulse onset detect is defined as being the point in time where the previous block was not detected as part of an impulse sequence, and an impulse is detected in the present block.
This is described as $$\text{onset} = \begin{cases} \text{true,} & \text{if (predetect == 0 \&\& detect == 1)} \\ \text{false,} & \text{otherwise} \end{cases} \quad (19)$$

Now, the algorithm can distinguish between impulse onset and the part of the impulse where all other conditions are still valid i.e. in the middle part of the impulse. The strategy for how to apply gain reduction is to use symmetric smoothing of the gain in blocks preceding the block where impulse onset is detected. The onset block will determine the gain starting point according to the current broadband power.

Short impulse-like signals are in some situations part of the spatial awareness experienced by the hearing impaired. In the sense that room reverberation is providing perceptual awareness about the characteristics and size of the room. Optimally, the gain reduction release time must be set according to the acoustic environment e.g. with respect to the reverberation time of the room, hall etc. The release time, in combination with the normal AGCI attack time, should be set so that the early reflections are still suppressed, while late reflections are perceived with normal loudness. For speech intelligibility, early reflections are very important for both normal hearing and hearing impaired persons, while the late reflections often degrades the ability to understand speech in noise. For impulse signals this is opposite, in the sense that late reflections adds to the perception of the room characteristics. For a hearing device user, early reflections, which could still include high energy at some frequencies, would still be over-amplified and though add to the discomfort (given that the AGCI release time is long compared to the arrival of the early reflections).

The sound impulse suppressor may have a broadband gain release time, i.e. all bands are adapted to the same time constants and this parameter is not adapted in any way during run-time. During the release time the gain reduction provided by the sound impulse suppressor will decade. This serves to smooth the transition between the sound impulse suppressor actively reducing the impact of the impulse, and restoring normal AGCI control of input related gain handling. The release of gain reduction will be based on a threshold on the detect parameter, FIG. 12A. This parameter can be used in the decision of when the impulse has decreased its strength to a point where it can be defined as completed. At this point the gain release takes over, FIGS. 12A and 12B illustrates the usage of a detection threshold.

A way of detecting and reacting upon impulsive inputs has been described in the previous sections. It is clear that input signals with impulsive onset and a certain length will have the ability to lock the detecting state of the algorithm. A measure of the duration of an impulse and a maximum impulse duration definition is needed. In order to hand-over signals that in nature exploits impulse start conditions, but are much longer in duration, the sound impulse suppressor is adapted to fade out and leave the gain handling to the normal warp compressor system. If a signal has impulsive onset followed by a long sequence with energy in many bands, the power estimation will, by design, be locked by the sound impulse detector. The consequence is that these types of sounds will be attenuated by the Gain Calculation block for much longer time that required, i.e. it will overlap with the normal warp compressor system which over time will reduce gains. E.g. the start of a lawnmower will typically go from a very quiet condition, over a short impulsive part and then stay noisy in many bands for a longer period. A definition of the maximum duration of the impulses the sound impulse suppressor should handle, and how to measure and fade-out is needed. A very elegant way of controlling the sound impulse detector part in relation to the duration of the impulse is to adaptively control the parameter in equation (3). Based on the information of where the current detection estimate is in time, it is possible to control the update rate of the frequency band power estimate smoothing. The flow-chart in FIG. 13 illustrates how to control and update the power estimator part of the detector. Based on a defined maximum duration count it is possible to decide the smoothing rate based on the parameter $\alpha$. An $\alpha$-value going towards zero will simply stop the smoothing of the frequency bands power estimates. This is the preferred setting in the sequence following the onset of an impulse, i.e. stop updating. For normal operation, where no impulse is detected a rather high value of $\alpha$ is needed in order to base the detection decision on the history of energy per bands. A fast power update is needed when the maximum duration of an impulse is reached. The consequence of lowering the $\alpha$-parameter, a fast update speed, will be that the power estimates will quickly adapt to the levels which is currently experienced by e.g. a lawnmower. The difference between the current estimate and the smoothed estimates will no longer exploit instant rise and the detection scheme will resign to release mode, and we can apply normal α values for a rather slow update rate again. The sequence of changing the α-parameter based on the detection value is shown in FIGS. 14A and 14B.

The sound impulse detector of each of the first hearing device and the second hearing device may be adjustable in accordance with the sound environment class determined by the binaural sound environment detector. FIG. 15 shows an exemplary plot of impulse gradient thresholds in dB along the y-axis for various sound environment classes along the x-axis.

At this point the differentiation in attenuation applied by the sound impulse suppressor is based purely on the broadband power. Gain vectors based on the prescribed gain are calculated on-line and applied according to the estimated broadband power. This scheme seems to favour the situations close to the $G_{50}$ knee-point, is could be an advantage to include another knee-point to reach a stage where the applied gain is steered towards the present sound pressure level. One solution could be to utilize the classifier classes which to some extend includes information about the sound pressure level of the environments. Table 3 below lists the sound pressure levels related to each of the classifier output classes. According to the table, it makes sense to add another gain table and base the calculated gain tables on a knee-point at approximately 75 $dB_{SPL}$. The classifier environments can now be used to steer the gain reduction tables in order to achieve that the sound impulse suppressor takes into account the current estimated sound environments. E.g. silent environments, where the prescribed gain are in the linear area, maps to higher gain reductions and high noise environments, where the gain operates in the compression area, should attend less gain reduction from the sound impulse suppressor.

TABLE 3

|   | Classifier Class | Sound Pressure Level |
| --- | --- | --- |
| 0 | Quiet | <50 dBSPL |
| 1 | Clean Speech Low | <60 dBSPL |
| 2 | Clean Speech High | >60 dBSPL |
| 3 | Speech In Noise Low | <75 dBSPL |
| 4 | Speech In Noise High | >75 dBSPL |
| 5 | Noise Low | <75 dBSPL |
| 6 | Noise High | >75 dBSPL |

According to another embodiment with a signal processing scheme shown in FIG. 16, e.g. for a hearing protection device, wherein the warped delay line and warped power estimates are not present, a more simple sound impulse detector and sound impulse suppressor can be utilized. In addition applications where the gain reduction is not to be associated with a hearing loss or prescribed gain, the impulse detection block of the sound impulse detector could provide input to a gain control unit rather than a gain calculation unit of the sound impulse suppressor. A gain control unit could control several parameters of the Gain controller given inputs from other gain agents and the Impulse Detection block.

Although particular embodiments have been shown and described, it will be understood that they are not intended to limit the claimed inventions, and it will be obvious to those skilled in the art that various changes and modifications may be made without departing from the spirit and scope of the claimed inventions. The specification and drawings are, accordingly, to be regarded in an illustrative rather than restrictive sense. The claimed inventions are intended to cover alternatives, modifications, and equivalents.

The invention claimed is:

1. A binaural hearing device system for a user, comprising:
    a first hearing device and a second hearing device, each of which comprises:
        at least one microphone for provision of an audio signal based on sound received at the at least one microphone in a sound environment;
        a signal processor that is configured to process the audio signal in accordance with a signal processing algorithm to generate a processed audio signal;
        a sound impulse detector configured to detect a presence of an impulse in the audio signal, and to output an impulse detected signal; and
        a receiver configured to provide an output sound signal based on the processed audio signal for emission towards an eardrum of the user of the binaural hearing device system; and
    a binaural impulse environment detector for binaural determination of a presence of an impulse environment surrounding the user of the binaural hearing device system based on the impulse detected signal of the sound impulse detector of the first hearing device and the impulse detected signal of the sound impulse detector of the second hearing device;
    wherein the binaural impulse environment detector is configured for provision of outputs for the first and second hearing devices for selection of the respective signal processing algorithms of the respective signal processors in the respective first and second hearing devices so that the first and second hearing devices perform coordinated processing of the audio signals.

2. The binaural hearing device system according to claim 1, further comprising a binaural sound environment detector for binaural determination of the sound environment surrounding the user of the binaural hearing device system.

3. The binaural hearing device system according to claim 2, wherein the binaural sound environment detector comprises the binaural impulse environment detector.

4. The binaural hearing device system according to claim 1, wherein the signal processor of the first hearing device comprises a sound impulse suppressor configured to attenuate the impulse in the audio signal of the first hearing device by signal processing parameter adjustment.

5. The binaural hearing device system according to claim 4, wherein the signal processing parameter adjustment is based on a user input.

6. The binaural hearing device system according to claim 1, wherein the sound impulse detector of the first hearing device is configured to divide the audio signal of the first hearing device into a plurality of frequency bands, and to detect the presence of the impulse in the audio signal of the first hearing device based on the frequency-divided audio signal.

7. The binaural hearing device system according to claim 1, wherein a signal processing parameter of the sound impulse detector of the first hearing device is adjustable in accordance with a user input.

8. A binaural hearing device system for a user, comprising:
    a first hearing device and a second hearing device, each of which comprises:
        at least one microphone for provision of an audio signal based on sound received at the at least one microphone in a sound environment;

a signal processor that is configured to process the audio signal in accordance with a signal processing algorithm to generate a processed audio signal;

a sound impulse detector configured to detect a presence of an impulse in the audio signal, and to output an impulse detected signal; and a receiver configured to provide an output sound signal based on the processed audio signal for emission towards an eardrum of the user of the binaural hearing device system: and a binaural impulse environment detector for binaural determination of a presence of an impulse environment surrounding the user of the binaural hearing device system based on the impulse detected signal of the sound impulse detector of the first hearing device and the impulse detected signal of the sound impulse detector of the second hearing device;

wherein the binaural hearing device system further comprises a binaural sound environment detector for binaural determination of the sound environment surrounding the user of the binaural hearing device system;

wherein the signal processor of the first hearing device comprises a sound impulse suppressor; and wherein at least one of the sound impulse detector and the sound impulse suppressor in the first hearing device is adjustable in accordance with a sound environment class determined by the binaural sound environment detector.

9. The binaural hearing device system according to claim 1, wherein the signal processor of each of the first hearing device and the second hearing device comprises a hearing loss processor configured to compensate a hearing loss of the user.

10. The binaural hearing device system according to claim 9, wherein the hearing loss processor of each of the first hearing device and the second hearing device comprises a dynamic range compressor configured to compensate the hearing loss including loss of dynamic range.

11. The binaural hearing device system according to claim 9, wherein the signal processor of each of the first hearing device and the second hearing device is configured to perform a gain adjustment based on a gain setting of the hearing loss processor of the respective one of the first hearing device and the second hearing device.

12. The binaural hearing device system according to claim 1, wherein each of the first hearing device and the second hearing device is a hearing protector comprising a passive dampener for dampening sound.

13. A method of binaural signal processing, comprising:
converting sound into a first audio signal and a second audio signal for respective ears of a user;
detecting a presence of an impulse in each of the first and second audio signals;
selecting signal processing algorithms for respectively processing the first audio signal and the second audio signal; and
processing each of the first and second audio signals into a processed audio signal in a coordinated manner based on the selected signal processing algorithms;
converting each of the processed signals into an output sound signal; and
emitting each of the output sound signals towards an eardrum of the user.

14. The method according to claim 13, further comprising reducing a gain of the processed audio signal in response to the detected presence of the impulse in each of the first and second audio signals.

15. The binaural hearing device system according to claim 1, wherein the sound impulse detector of the first hearing device is configured to distinguish speech from impulse sound.

16. The binaural hearing device system according to claim 1, wherein the binaural hearing device system is configured to attenuate a detected impulse detected by the sound impulse detector of the first hearing device.

17. The binaural hearing device system according to claim 1, wherein the sound impulse detector of the first hearing device is adjustable.

18. The binaural hearing device system according to claim 1, wherein the sound impulse detector of the first hearing device has a broadband gain release time.

19. The method according to claim 13, further comprising distinguishing speech from impulse sound.

20. The method according to claim 13, further comprising attenuating a detected impulse detected in the first audio signal.

21. The method according to claim 13, wherein the presence of the impulse is detected by a sound impulse detector that is adjustable.

22. The method according to claim 13, wherein the presence of the impulse is detected by a sound impulse detector that has a broadband gain release time.

23. A binaural hearing device system for a user, comprising:
a first hearing device and a second hearing device, wherein the first hearing device comprises:
at least one microphone for provision of an audio signal based on sound received at the at least one microphone in a sound environment;
a signal processor that is configured to process the audio signal in accordance with a signal processing algorithm to generate a processed audio signal;
a sound impulse detector configured to detect a presence of an impulse in the audio signal, and to output an impulse detected signal; and
a receiver configured to provide an output sound signal based on the processed audio signal for emission towards an eardrum of the user of the binaural hearing device system; and
a binaural impulse environment detector for binaural determination of a presence of an impulse environment surrounding the user of the binaural hearing device system based on the impulse detected signal;
wherein the binaural impulse environment detector is configured for provision of an output for the first hearing device for selection of the signal processing algorithm so that the first hearing device performs coordinated signal processing with respect to a signal processing by the second hearing device.

24. The binaural hearing device system according to claim 23, further comprising a binaural sound environment detector for binaural determination of the sound environment surrounding the user of the binaural hearing device system.

25. The binaural hearing device system according to claim 24, wherein the binaural sound environment detector comprises the binaural impulse environment detector.

26. The binaural hearing device system according to claim 23, wherein the signal processor of the first hearing device comprises a sound impulse suppressor configured to attenuate the impulse in the audio signal of the first hearing device by signal processing parameter adjustment.

27. The binaural hearing device system according to claim 26, wherein the signal processing parameter adjustment is based on a user input.

28. The binaural hearing device system according to claim 23, wherein the sound impulse detector of the first hearing device is configured to divide the audio signal of the first hearing device into a plurality of frequency bands, and to detect the presence of the impulse in the audio signal of the first hearing device based on the frequency-divided audio signal.

29. The binaural hearing device system according to claim 23, wherein a signal processing parameter of the sound impulse detector of the first hearing device is adjustable in accordance with a user input.

30. The binaural hearing device system according to claim 23, wherein the signal processor of the first hearing device comprises a hearing loss processor configured to compensate a hearing loss of the user.

31. The binaural hearing device system according to claim 23, wherein the first hearing device is a hearing protector comprising a passive dampener for dampening sound.

32. The binaural hearing device system according to claim 23, wherein the sound impulse detector of the first hearing device is configured to distinguish speech from impulse sound.

33. The binaural hearing device system according to claim 23, wherein the binaural hearing device system is configured to attenuate a detected impulse detected by the sound impulse detector of the first hearing device.

34. The binaural hearing device system according to claim 23, wherein the sound impulse detector of the first hearing device is adjustable.

35. The binaural hearing device system according to claim 23, wherein the sound impulse detector of the first hearing device has a broadband gain release time.

* * * * *